(12) United States Patent
Peterson et al.

(10) Patent No.: US 11,237,147 B2
(45) Date of Patent: Feb. 1, 2022

(54) METHODS FOR USING ISOTOPIC SIGNATURES TO DETERMINE CHARACTERISTICS OF HYDROCARBON SOURCES

(71) Applicants: Brian K. Peterson, Fogelsville, PA (US); Michael Lawson, Spring, TX (US); Michael J. Formolo, The Woodlands, TX (US); Meytal B. Higgins, Princeton, NJ (US)

(72) Inventors: Brian K. Peterson, Fogelsville, PA (US); Michael Lawson, Spring, TX (US); Michael J. Formolo, The Woodlands, TX (US); Meytal B. Higgins, Princeton, NJ (US)

(73) Assignee: ExxonMobil Upstream Research Company, Spring, TX (US)

( * ) Notice: Subject to any disclaimer, the term of this patent is extended or adjusted under 35 U.S.C. 154(b) by 743 days.

(21) Appl. No.: 15/971,691

(22) Filed: May 4, 2018

(65) Prior Publication Data
US 2018/0321215 A1 Nov. 8, 2018

Related U.S. Application Data

(60) Provisional application No. 62/503,113, filed on May 8, 2017.

(51) Int. Cl.
*G01N 33/24* (2006.01)
*G01V 9/00* (2006.01)
(Continued)

(52) U.S. Cl.
CPC ............ *G01N 33/241* (2013.01); *E21B 47/11* (2020.05); *G01N 33/2823* (2013.01);
(Continued)

(58) Field of Classification Search
CPC .. G01N 33/241; G01N 33/2823; G01N 29/14; E21B 47/11; G01V 9/007; G01V 2210/1234
See application file for complete search history.

(56) References Cited

U.S. PATENT DOCUMENTS 8,316,934 B2 11/2012 Pietrobon
9,594,879 B2 3/2017 Eiler
(Continued)

FOREIGN PATENT DOCUMENTS

JP   H10311882 A   11/1998
JP   2004536321 A   12/2004
(Continued)

OTHER PUBLICATIONS

Piasecki "Prediction of equilibrium distributions of isotopologues for methane, ethane and propane using density functional theory." (Year: 2016).*

(Continued)

*Primary Examiner* — Regis J Betsch
*Assistant Examiner* — Kaleria Knox
(74) *Attorney, Agent, or Firm* — ExxonMobil Upstream Research Company—Law Department

(57) ABSTRACT

Described herein are methods and techniques for determining one or more characteristics of a hydrocarbon source. The method comprises obtaining a hydrocarbon fluid sample, determining at least one measured clumped isotope signature or measured position specific isotope signature for at least one hydrocarbon species of interest in the hydrocarbon fluid sample, determining at least one expected clumped isotope signature or expected position specific isotope signature for the hydrocarbon species of interest, comparing the measured clumped isotope signature or measured position specific isotope signature with the expected clumped isotope (Continued)

signature or expected position specific isotope signature, and determining at least one characteristic of the source of the hydrocarbon sample based on the comparison.

15 Claims, 12 Drawing Sheets

(51) Int. Cl.
    *G01N 33/28*     (2006.01)
    *E21B 47/11*     (2012.01)
    *G01N 29/14*     (2006.01)

(52) U.S. Cl.
    CPC ............. *G01V 9/007* (2013.01); *G01N 29/14* (2013.01); *G01V 2210/1234* (2013.01)

(56) References Cited

U.S. PATENT DOCUMENTS

| | | |
|---|---|---|
| 2004/0166582 A1 | 8/2004 | Prinzhofer et al. |
| 2010/0326651 A1* | 12/2010 | Pietrobon ................ E21B 43/14 166/250.01 |
| 2011/0301866 A1* | 12/2011 | Holba ..................... E21B 47/10 702/24 |
| 2014/0097338 A1 | 4/2014 | Eiler |
| 2014/0250999 A1* | 9/2014 | Lawson .................. E21B 49/02 73/152.23 |
| 2014/0256055 A1 | 9/2014 | Pottorf et al. |
| 2014/0288853 A1 | 9/2014 | Dreyfus et al. |
| 2014/0303895 A1 | 10/2014 | Dreyfus et al. |
| 2015/0127313 A1* | 5/2015 | Lawson .................. E21B 43/16 703/10 |
| 2016/0084045 A1 | 3/2016 | Lawson et al. |
| 2016/0084080 A1 | 3/2016 | Lawson et al. |
| 2016/0084081 A1 | 3/2016 | Lawson et al. |
| 2016/0084817 A1 | 3/2016 | Lawson et al. |
| 2016/0222781 A1 | 8/2016 | Lawson et al. |
| 2016/0222782 A1 | 8/2016 | Lawson et al. |
| 2016/0258922 A1 | 9/2016 | Formolo et al. |

FOREIGN PATENT DOCUMENTS

| | | |
|---|---|---|
| JP | 2007033076 A | 2/2007 |
| JP | 2007319808 A | 12/2007 |
| JP | 2009538908 A1 | 11/2009 |
| WO | WO 2007/008932 A2 | 1/2007 |
| WO | 2007142864 A2 | 12/2007 |

OTHER PUBLICATIONS

Batttaile "The Kinetic Monte Carlo method: Foundation, implementation, and application". (Year: 2013).*
Stolper "Distinguishing and understanding thermogenic and biogenic sources of methane using multiply substituted isotopologue". (Year: 2015).*
Corbett C. Battaile "The Kinetic Monte Carlo method: Foundation, implementation and application" (Year: 2008).*
Battaile (2008) "The Kinetic Monte Carlo Method: Foundation, Implementation, and Application", Computer Methods in Applied Mechanics and Engineering, vol. 197, pp. 3386-3398.
Bernard (1979) "Methane in Marine Sediments", Deep-Sea Research, vol. 26A, pp. 429-443.
Bernard et al. (1978) "Light Hydrocarbons in Recent Texas Continental Shelf and Slope Sediments", Journal of Geophysical Research, vol. 83, pp. 4053-4061.
Berner et al. (1988) "Maturity Related Mixing Model for Methane, Ethane and Propane, Based on Carbon Isotopes", Advances in Organic Geochemistry 1987, Org. Geochem., vol. 13, pp. 67-72.
Berner et al. (1995) "Primary cracking of algal and landplant kerogens: kinetic models of isotope variations in methane, ethane and propane", Chemical Geology, vol. 126, pp. 233-245.

Bounaceur et al. (2002) "Modeling of hydrocarbons pyrolysis at low temperature. Automatic generation of free radicals mechanisms.", Journal of Analytical and Applied Pyrolysis, vol. 64, pp. 103-122.
Braun et al. (1990) "Mathematical Model of Oil Generation, Degradation, and Expulsion", Energy & Fuels, vol. 4, pp. 132-146.
Burklé-Vitzthum et al. (2011) "Thermal evolution of n- and iso-alkanes in oils. Part 1: Pyrolysis model for a mixture of 78 alkanes ($C_1$-$C_{32}$) including 13,206 free radical reactions", Organic Geochemistry, vol. 42, pp. 439-450.
Burnham (1989) "A simple kinetic model of petroleum formation and cracking", Lawrence Livermore National Lab Technical Report UCID-21665.
Chung et al. (1979) "Use of Stable Carbon Isotope Compositions of Pyrolytically Derived Methane as Maturity Indices for Carbonaceous Materials", Geochimica et Cosmochimica Acta, vol. 43, pp. 1979-1988.
Chung et al. (1980) "Carbon isotope effects during the pyrolytic formation of early methane from carbonaceous materials", Physics and Chemistry of the Earth, vol. 12, pp. 705-710.
Chung et al. (1988) "Origin of Gaseous Hydrocarbons in Subsurface Environments: Theoretical Considerations of Carbon Isotope Distribution", Chemical Geology, vol. 71, pp. 97-103.
Clayton (1991) "Carbon isotope fractionation during natural gas generation from kerogen", Marine and Petroleum Geology, vol. 8, pp. 232-240.
Clog et al. (2018) "A reconnaissance study of $^{13}C$-$^{13}C$ clumping in ethane from natural gas", Geochimica et Cosmochimica Acta, vol. 223, pp. 229-244.
Cramer et al. (1998) "Modelling isotope fractionation during primary cracking of natural gas: a reaction kinetic approach", Chemical Geology, vol. 149, pp. 235-250.
Cramer et al. (2001) "Reaction Kinetics of Stable Carbon Isotopes in Natural Gas—Insights from Dry, Open System Pyrolysis Experiments", Energy & Fuels, vol. 15, pp. 517-532.
Amar, J. G. (2006) "The Monte Carlo Method in Science and Engineering", Computing in Science & Engineering, Mar. 1, 2006, vol. 8(2), pp. 9-19 XP055580281.
Webb et al., "Position-Specific and Clumped Stable Isotope Studies: Comparison of the Urey and Path-Integral Approaches for Carbon Dioxide, Nitrous Oxide, Methane, and Propane", The Journal of Physical Chemistry A., Dec. 27, 2013, p. 467-474.
Piasecki et al. (2016) "Prediction of Equilibrium Distributions of Isotopologues for Methane, Ethane and Propane Using Density Functional Theory", Geochimica et Cosmochimica Acta, Pergamon Press, New York, NY, vol. 190, Jun. 23, 2016, pp. 1-12 (XP029704844).
Stolper et al. (2015) "Distinguishing and Understanding Thermogenic and Biogenic Sources of Methane Using Multiply Substituted Isotopologues", Geochimica et Cosmochimica Acta, Pergamon Press, New York, NY, vol. 161, Apr. 17, 2015, pp. 219-247 (XP029185726).
Douglas et al. (2017) "Methane clumped isotopes: Progress and potential for a new isotopic tracer", Organic Geochemistry, vol. 113, pp. 262-282.
Eiler (2007) ""Clumped-Isotope" geochemistry—The study of naturally-occurring, multiply-substituted isotopologues". Earth and Planetary Science Letter, vol. 262, pp. 309-327.
Eiler et al. (2004) "$^{18}O^{13}C^{16}O$ in Earth's atmosphere", Geochimica et Cosmochimica Acta, vol. 68, pp. 4767-4777.
Fichthorn et al. (1991) "Theoretical foundations of dynamical Monte Carlo simulations", The Journal of Chemical Physics, vol. 95, pp. 1090-1096.
Galimov (2006) "Isotope organic geochemistry", Organic Geochemistry, vol. 37, pp. 1200-1262.
Galimov et al. (1973) "Thermodynamic Isotope Effects in Organic Compounds; 1. Carbon Isotope Effects in Straight-chain Alkanes", Russian Journal of Physical Chemistry, vol. 47, Issue 11, pp. 1564-1566.
Gao et al. (2016) "Determination of position-specific carbon isotope ratios in propane from hydrocarbon gas mixtures", Chemical Geology, vol. 435, pp. 1-9.
Gao et al. (2016) "Reaction Mechanism Generator: Automatic construction of chemical kinetic mechanisms", Computer Physics Communications, vol. 203, pp. 212-225.

(56) References Cited

OTHER PUBLICATIONS

Gilbert et al. (2013) "Exploration of intramolecular $^{13}C$ isotope distribution in long chain n-alkanes ($C_{11}$-$C_{31}$) using isotopic $^{13}C$ NMR", Organic Geochemistry, vol. 62, pp. 56-61.
Gilbert et al. (2016) "Measurement of position-specific $^{13}C$ isotopic composition of propane at the nanomole level", Geochimica et Cosmochimica Acta, vol. 177, pp. 205-216.
Gillespie (1977) "Exact Stochastic Simulation of Coupled Chemical Reactions", The Journal of Physical Chemistry, vol. 81, pp. 2340-2361.
Hellekalek (1998) "Don't Trust Parallel Monte Carlo!", ACM SIGSIM Simulation Digest, vol. 28, pp. 82-89.
Hinrichs et al. (2006) "Biological formation of ethane and propane in the deep marine subsurface", Proceedings of the National Academy of Sciences of the United States of America, vol. 103, pp. 14684-14689.
Hohl et al. (2010) "Energy, Environment and Climate Directorate White Paper", DCO Energy, Environment and Climate Workshop, pp. 1-38.
James (1983) "Correlation of natural gas by use of carbon isotopic distribution between hydrocarbon components" AAPG Bulletin, vol. 67, pp. 1176-1191.
James (1990) "Correlation of Reservoired Gases Using the Carbon Isotopic Compositions of Wet Gas Components", AAPG Bulletin, vol. 74, No. 9, pp. 1441-1458.
Kossiakoff et al. (1943) "Thermal Decomposition of Hydrocarbons, Resonance Stabilization and Isomerization of Free Radicals", Journal of the American Chemical Society, vol. 65, pp. 590-595.
Lewan (1983) "Effects of thermal maturation on stable organic carbon isotopes as determined by hydrous pyrolysis of Woodford Shale", Geochimica et Cosmochimica Acta, vol. 47, pp. 1471-1479.
Lewan (1985) "Evaluation of Petroleum Generation by Hydrous Pyrolysis Experimentation", Philosophical Transactions of the Royal Society of London A, vol. 315, pp. 123-134.
Lorant et al. (1998) "Carbon isotopic and molecular constraints on the formation and the expulsion of thermogenic hydrocarbon gases", Chemical Geology, vol. 147, pp. 249-264.
O'Neill (2014) "PCG: A Family of Simple Fast Space-Efficient Statistically Good Algorithms for Random Number Generation".
Pepper et al. (1995) "Simple kinetic models of petroleum formation. Part I: oil and gas generation from kerogen", Marine and Petroleum Geology, vol. 12, pp. 291-319.
Pepper et al. (1995) "Simple kinetic models of petroleum formation. Part II: oil-gas cracking", Marine and Petroleum Geology, vol. 12, pp. 321-340.
Piasecki et al. (2016) "Analysis of the site-specific carbon isotope composition of propane by gas source isotope ratio mass spectrometer", Geochimica et Cosmochimica Acta, vol. 188, pp. 58-72.
Piasecki et al. (2018) "Position-specific $^{13}C$ distributions within propane from experiments and natural gas samples", Geochimica et Cosmochimica Acta, vol. 220, pp. 110-124.
Plimpton et al. (2009) "Crossing the Mesoscale No-Man's Land via Parallel Kinetic Monte Carlo", Sandia Report SAND2009-6226, pp. 1-82.
Rice et al. (1981) "Generation, accumulation, and resource potential of biogenic gas", AAPG Bulletin, vol. 65, pp. 5-25.
Rooney et al. (1995) "Modeling thermogenic gas generation using carbon isotope ratios of natural gas hydrocarbons", Chemical Geology, vol. 126, pp. 219-232.
Sackett (1978) "Carbon and hydrogen isotope effects during the thermocatalytic production of hydrocarbons in laboratory simulation experiments", Geochimica et Cosmochimica Acta, vol. 42, pp. 571-580.
Savage (2000) "Mechanisms and kinetics models for hydrocarbon pyrolysis", Journal of Analytical and Applied Pyrolysis, vol. 54, pp. 109-126.
Schoell (1980) "The hydrogen and carbon isotopic composition of methane from natural gases of various origins", vol. 44, pp. 649-661.

Sherwood Lollar et al. (2001) "Abiogenic formation of alkanes in the Earth's crust as a minor source for global hydrocarbon reservoirs", Nature, vol. 416, pp. 522-524.
Shuai et al. (2018) "Methane clumped isotopes in the Songliao Basin (China): New insights into abiotic vs. biotic hydrocarbon formation", Earth and Planetary Science Letters, vol. 482, pp. 213-221.
Stahl (1977) "Carbon and Nitrogen Isotopes in Hydrocarbon Research and Exploration", Chemical Geology, vol. 20, pp. 121-149.
Stolper (2014) "New Insights Into the Formation and Modification of Carbonate-Bearing Minerals and Methane Gas in Geological Systems Using Multiply Substituted Isotopologues", Thesis at California Institute of Technology, pp. 1-305.
Stolper et al. (2014) "Formation temperatures of thermogenic and biogenic methane", Science, vol. 344, pp. 1500-1503.
Stolper et al. (2017) "The utility of methane clumped isotopes to constrain the origins of methane in natural gas accumulations", *From Source to Seep: Geochemical Applications in Hydrocarbon Systems*, Geological Society, London, Special Publications, pp. 1-30.
Suda et al. (2017) "Compound- and position-specific carbon isotopic signatures of abiogenic hydrocarbons from on-land serpentinite-hosted Hakuba Happo hot spring in Japan", Geochimica et Cosmochimica Acta, vol. 206, pp. 201-215.
Sundaram et al. (1978) "Modeling of Thermal Cracking Kinetics. 3. Radical Mechanisms for the Pyrolysis of Simple Paraffins, Olefins, and Their Mixtures", Industrial & Engineering Chemistry Fundamentals, vol. 17, pp. 174-182.
Tang et al. (1995) "Theoretical Modeling of Carbon and Hydrogen Isotope Fractionation in Natural Gas", Organic Geochemistry, Developments and Applications to Energy, Climate, Environment and Human History, AIGOA, pp. 1067-1069.
Tang et al. (2000) "Mathematical modeling of stable carbon isotope ratios in natural gases", Geochimica et Cosmochimica Acta, vol. 64, pp. 2673-2687.
Tang et al. (2005) "A kinetic model for thermally induced hydrogen and carbon isotope fractionation of individual n-alkanes in crude oil", Geochimica et Cosmochimica Acta, vol. 69, pp. 4505-4520.
Tissot et al. (1978) "Petroleum Formation and Occurrence: A New Approach to Oil and Gas Exploration", Springer-Verlag Berlin Heidelberg.
Vandenbroucke et al. (1999) "Kinetic modelling of petroleum formation and cracking: implications from the high pressure/high temperature Elgin Field (UK, North Sea)", Organic Geochemistry, vol. 30, pp. 1105-1125.
Voge et al. (1949) "Thermal Cracking of Higher Paraffins", Journal of the American Chemical Society, vol. 71, pp. 593-597.
Voter (2007) "Introduction to the Kinetic Monte Carlo Method", Radiation Effects in Solids, NATO Science Series, vol. 235, pp. 1-23.
Walters et al. (2007) "Predicting oil and gas compositional yields via chemical structure-chemical yield modeling (CS-CYM): Part 2—Application under laboratory and geologic conditions", Organic Geochemistry, vol. 38, pp. 306-322.
Wang et al. (2015) "Nonequilibirum clumped isotope signals in microbial methane", Science, vol. 348, pp. 428-431.
Westbrook et al. (2009) "A comprehensive detailed chemical kinetic reaction mechanism for combustion of n-alkane hydrocarbons from n-octane to n-hexadecane", Combustion and Flame, vol. 156, pp. 181-199.
Whiticar (1994) "Correlation of Natural Gases with their Sources", The Petroleum System—from Source to Trap, AAPG Memoir, pp. 261-283.
Whiticar (1996) "Stable isotope geochemistry of coals, humic kerogens and related natural gases", International Journal of Coal Geology, vol. 32, pp. 191-215.
Xiao (2001) "Modeling the Kinetics and Mechanisms of Petroleum and Natural Gas Generation: A First Principles Approach", Reviews in Mineralogy and Geochemistry, vol. 42, pp. 383-436.
Xiao et al. (2009) "Tracing of deeply-buried source rock: A case study of the WC9-2 petroleum pool in the Pearl River Mouth Basin, South China Sea", Marine and Petroleum Geology, vol. 26, Issue 8, pp. 1365-1378.

(56) References Cited

OTHER PUBLICATIONS

Xiong et al. (2016) "The origin and evolution of thermogenic gases in organic-rich marine shales", Journal of Petroleum Science and Engineering, vol. 143, pp. 8-13.

Young et al. (2017) "The relative abundances of resolved $^{12}CH_2D_2$ and $^{13}CH_3D$ and mechanisms controlling isotopic bond ordering in abiotic and biotic methane gases", Geochimica et Cosmochimica Acta, vol. 203, pp. 235-264.

\* cited by examiner

METHODS FOR USING ISOTOPIC SIGNATURES TO DETERMINE CHARACTERISTICS OF HYDROCARBON SOURCES

CROSS-REFERENCE TO RELATED APPLICATIONS

This application claims the benefit of U.S. Provisional Application Ser. No. 62/503,113 filed May 8, 2017, the disclosure of which is incorporated herein by reference in its entirety.

FIELD OF THE INVENTION

Described herein are methods that utilize isotopic signatures, such as clumped isotope signatures and/or position specific isotope signatures, to determine characteristics of hydrocarbon sources.

BACKGROUND

Hydrocarbons are generated in the subsurface from source rocks rich in organic matter. Following initial deposition, source rocks are buried and subjected to increasing temperature and pressure with increasing burial. Hydrocarbons are then generated when the source rocks reach temperatures sufficient for thermal conversion of the organic matter into kerogen and then to free liquid and/or gaseous hydrocarbon phases in a process called source rock maturation. Upon generation, the hydrocarbons may subsequently be expulsed from the source rock and migrated in the subsurface to reservoir rocks (such as sandstones or carbonates) that have sufficient porosity, structure, and an adequate seal that make them capable of trapping the hydrocarbon phase(s), allowing hydrocarbons to accumulate. Alternatively, hydrocarbons may migrate to a surface location (e.g., a seep). Hydrocarbons present in the subsurface may be preserved or they may be subjected to different forms of alteration. For example, biodegradation is the process of degradation or consumption of hydrocarbons by microorganisms. Similarly, hydrocarbons may be thermally altered by exposure to temperatures above their thermal stability. Alternatively, hydrocarbons may be oxidized or consumed in processes, such as thermochemical sulfate reduction.

There are many important geologic factors that can influence the occurrence of hydrocarbon accumulations in the subsurface. For example, the type of organic source matter and the thickness, quality, and thermal history of a given source interval can influence the volume of hydrocarbons that are generated and the likely distribution of the type of hydrocarbons generated (e.g., oil vs. gas). Therefore, knowledge of the type of organic source matter (e.g., terrestrial, marine, and/or lacustrine) and knowledge of the stratigraphic interval of the source rock can significantly enhance one's understanding of the hydrocarbon system, and such information can be used to improve hydrocarbon exploration operations on both a local and regional basis.

Conventional hydrocarbon exploration, development, and production operations have used various geochemical techniques to attempt to estimate the maturity of the source rock from which the hydrocarbons were generated, to estimate the source facies from which the hydrocarbons were generated (e.g., marine or terrestrial source rocks), to estimate the age of the source rock, to differentiate between different potential origins of hydrocarbons (e.g., biogenic or thermogenic), and to provide information on hydrocarbon alteration.

For example, a series of hydrocarbon composition and stable isotope models have been developed to estimate thermal maturity and identify alteration in hydrocarbon gases. See e.g., W. J. Stahl, (1977) "Carbon and Nitrogen Isotopes in Hydrocarbon Research and Exploration", *Chemical Geology*, Vol. 20, pp. 121-149; Berner et al., (1988) "Maturity Related Mixing Model for Methane, Ethane and Propane, Based on Carbon Isotopes", *Advances in Organic Geochemistry*, Vol. 13, pp. 67-72; Chung et al., (1979) "Use of Stable Carbon Isotope Compositions of Pyrolytically Derived Methane as Maturity Indices for Carbonaceous Materials", *Geochimica et Cosmochimica Acta*, Vol. 43, pp. 1979-1988; A. T. James, (1990) "Correlation of Reservoired Gases Using the Carbon Isotopic Compositions of Wet Gas Components", *AAPG Bulletin*, Vol. 74, No. 9, pp. 1441-1458; and M. J. Whiticar, (1996) "Stable isotope geochemistry of coals, humic kerogens and related natural gases", *International Journal of Coal Geology*, Vol. 32, pp. 191-215.

As another example, U.S. Patent Application Publication No. 2015/0127313 describes measuring a clumped isotope signature from a hydrocarbon sample from a hydrocarbon seep and comparing the measured signature to an expected signature, where the expected signature is one that was modeled using a temperature-dependent stochastic distribution of isotopologues. The comparison is then used to estimate a storage temperature of the hydrocarbons, and the storage temperature is then used to estimate a location (e.g., depth) of the subsurface accumulation from which the hydrocarbons seeped. Similarly, U.S. Patent Application Publication No. 2016/0084080 describes using a multiply substituted isotopologue signature or a position specific isotope signature to determine an alteration timing of the hydrocarbons.

However, such conventional methods often cannot provide the level of detail needed to directly link the hydrocarbon source facies to the reservoired or seeped hydrocarbons. Thus, there remains a need for methods and techniques to link and/or correlate hydrocarbon sources to reservoired or seeped hydrocarbons. Further, it would be desirable to have methods and systems that allow for the prediction of the reaction progress (e.g., hydrocarbon generation rate) and/or the determination of the maturity, age, amount of mixing and alteration of the starting hydrocarbon source material from a sample of a seeped or reservoired hydrocarbon fluid.

Background references may include U.S. Patent Application Publication Nos. 2014/0097338, 2014/0250999, 2014/0256055, 2014/0288853, 2014/0303895, 2016/0084817, 2016/0084045, 2016/0084081, 2016/0222781, 2016/0222782, and 2016/0258922; U.S. Pat. Nos. 8,316,934 and 9,594,879; PCT Publication No. WO 2007/008932; Hohl et al. (2010), "Energy, Environment and Climate Directorate White Paper", *DCO Energy, Environment and Climate Workshop*, pp. 1-38; Gao et al. (2016), "Determination of position-specific carbon isotope ratios in propane from hydrocarbon gas mixtures", *Chemical Geology*, Vol. 435, pp. 1-9; Gilbert et al. (2016), "Measurement of position-specific $^{13}C$ isotopic composition of propane at the nanomole level", *Geochimica et Cosmochimica Acta*, Vol. 177, pp. 205-216; J. M. Eiler (2007), ""Clumped-Isotope" geochemistry—The study of naturally-occurring, multiply-substituted isotopologues", *Earth and Planetary Science Letter*, Vol. 262, pp. 309-327; Piasecki et al. (2016), "Analysis of the site-specific carbon isotope composition of propane by gas source isotope ratio mass spectrometer", *Geochimica et Cosmochimica Acta*, Vol. 188, pp. 58-72; D. A. Stopler (2014), "New Insights Into the Formation and Modification of Carbonate-Bearing Minerals and Methane Gas in Geological Systems Using Multiply Substituted Isotopologues", Thesis at California Institute of Technology, pp. 1-305; and Xiao et al. (2009), "Tracing of deeply-buried source rock: A case study of the WC9-2 petroleum pool in the Pearl River Mouth Basin, South China Sea", *Marine and Petroleum Geology*, Vol. 26, pp. 1365-1378.

SUMMARY

Described herein are methods and techniques for determining one or more characteristics of a hydrocarbon source. The method comprises obtaining a hydrocarbon fluid sample, determining at least one measured clumped isotope signature or measured position specific isotope signature for at least one hydrocarbon species of interest in the hydrocarbon fluid sample, determining at least one expected clumped isotope signature or expected position specific isotope signature for the hydrocarbon species of interest, comparing the measured clumped isotope signature or measured position specific isotope signature with the expected clumped isotope signature or expected position specific isotope signature, and determining at least one characteristic of the source of the hydrocarbon sample based on the comparison.

DETAILED DESCRIPTION OF THE DISCLOSURE

Figure 1:
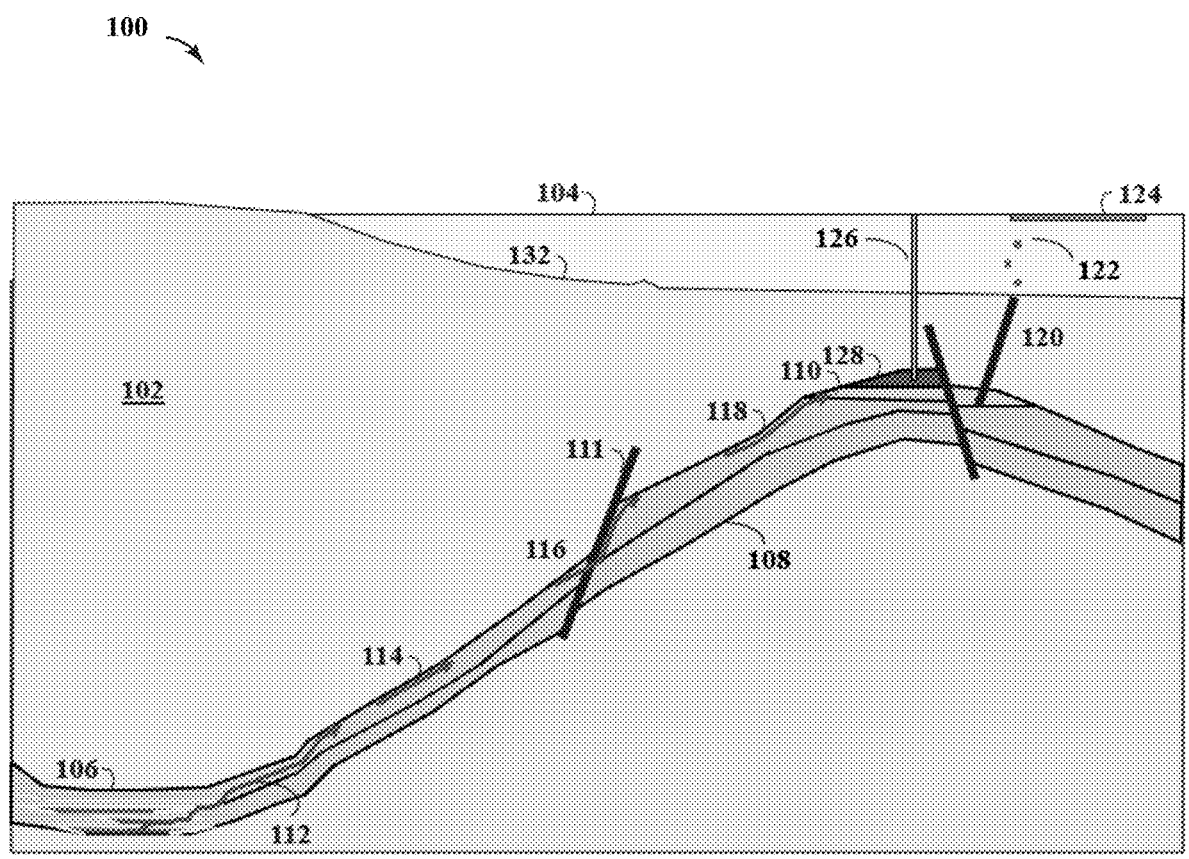
FIG. 1 is a side elevation view of components of a hydrocarbon system in a subsurface region.

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention can be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

Various terms as used herein are defined below. To the extent a term used in a claim is not defined below, it should be given the broadest possible definition persons in the pertinent art have given that term as reflected in at least one printed publication or issued patent.

As used herein, the term "basin modeling" refers generally to any method or analysis which provides a representation of the history of a sedimentary basin or other subsurface section of interest and/or an estimate of timing of any component of a hydrocarbon system. For example, a basin model may be used to model, but is not limited to, a burial history, time a specific subsurface location or layer reached a certain temperature or maturity, time for how long a location was in a certain temperature range, timing of expulsion, timing of migration, and/or timing of accumulation. Generally a basin model is based on and/or constrained by measured or derived data representing present day conditions (e.g., stratigraphy, current bottom hole temperature, heat flow) or a condition in the past (e.g., water depth) on which a model of the past history of the area of interest is based. The calculations used to form the basin model may be performed using a processor or other computer system.

As used herein, "exemplary" means serving as an example, instance, or illustration. Any embodiment described herein as exemplary is not to be construed as preferred or advantageous over other embodiments.

As used herein, "hydrocarbons" are generally defined as molecules formed primarily of carbon and hydrogen atoms such as oil and natural gas. Hydrocarbons may also include other elements or compounds, such as, but not limited to, halogens, metallic elements, nitrogen, oxygen, sulfur, hydrogen sulfide (H$_2$S), and carbon dioxide (CO$_2$). Hydrocarbons may be produced from hydrocarbon reservoirs through wells penetrating a hydrocarbon containing formation. Hydrocarbons derived from a hydrocarbon reservoir may include, but are not limited to, petroleum, kerogen, bitumen, pyrobitumen, asphaltenes, tars, oils, natural gas, or combinations thereof.

As used herein, "hydrocarbon development" refers to any activity associated with planning of extraction and/or access to hydrocarbons in subsurface regions. Hydrocarbon development normally refers to any activity conducted to plan for access to and/or for production of hydrocarbons from the subsurface formation and the associated modeling of the data to identify preferred development approaches and methods. By way of example, hydrocarbon development may include modeling of the subsurface formation and extracting planning for periods of production, determining and planning equipment to be utilized and techniques to be utilized in extracting the hydrocarbons from the subsurface formation, and the like.

As used herein, "hydrocarbon exploration" refers to any activity associated with determining the location of hydrocarbons in subsurface regions. Hydrocarbon exploration normally refers to any activity conducted to obtain measurements through acquisition of measured data associated with the subsurface formation and the associated modeling of the data to identify potential locations of hydrocarbon accumulations. Accordingly, hydrocarbon exploration includes acquiring measurement data, modeling of the measurement data to form subsurface models, and determining the likely locations for hydrocarbon reservoirs within the subsurface. The measurement data may include seismic data, gravity data, magnetic data, electromagnetic data, and the like.

As used herein, "hydrocarbon operations" refers to any activity associated with hydrocarbon exploration, hydrocarbon development, and/or hydrocarbon production. For example, hydrocarbon operations may comprise hydrocarbon management or managing hydrocarbons, which may include hydrocarbon extraction, hydrocarbon production, hydrocarbon exploration, identifying potential hydrocarbon resources, identifying potential well locations (such as injection and/or production wells), determining well injection and/or extraction rates, identifying reservoir connectivity, acquiring hydrocarbon resources, disposing of and/or abandoning hydrocarbon resources, reviewing prior hydrocarbon management decisions, and any other hydrocarbon related acts or activities.

As used herein, "hydrocarbon production" or "producing hydrocarbons" refers to any activity associated with extracting hydrocarbons from a well or other opening. Hydrocarbon production normally refers to any activity conducted to form the wellbore along with any activity in or on the well after the well is completed. Accordingly, hydrocarbon production or extraction includes not only primary hydrocarbon extraction but also secondary or tertiary production techniques, such as injection of gas or liquid for increasing drive pressure, mobilizing the hydrocarbon or treating the well by, for example chemicals, hydraulic fracturing of the well to promote increased flow, well servicing, well logging, and other well and wellbore treatments.

As used herein, the term "isotope" refers to one of two or more atoms with the same atomic number but with different numbers of neutrons. Hydrocarbon molecules generally contain both carbon and hydrogen atoms and may contain a variety of isotopes. For example, each carbon atom in a hydrocarbon molecule can be present as one of two stable isotopes: $^{12}C$, which has 6 protons and 6 neutrons, or $^{13}C$, which has 6 protons and 7 neutrons. Similarly, each hydrogen atom in a hydrocarbon molecule can be present as one of two stable isotopes: H, which contains 1 proton and no neutrons, or deuterium (D), which has 1 proton and 1 neutron.

As used herein, the term "isotopologues" refers generally to molecules that have the same chemical composition, but have a different isotopic signature. For example, methane contains one atom of carbon and four atoms of hydrogen; thus, each atom in the methane structure can contain one of the two stable isotopes of that atom, and as such there are ten possible isotopologues of methane.

As used herein, the term "multiply substituted isotopologues" refers generally to an isotopologue that contains at least two rare isotopes in its structure. For example, a multiply substituted methane isotopologue may contain one $^{13}C$ atom and one D atom, or at least two D atoms and no $^{13}C$ atom.

As used herein, the term "clumped isotopologue" refers generally to an isotopologue that contains at least two rare isotopes that share a common chemical bond in its structure. For example, a clumped isotopologue of methane contains one $^{13}C$ atom that shares a chemical bond with at least one D atom.

As used herein, the term "position specific isotope signature" refers generally to a compound that has multiple chemically or structurally distinct positions for a rare isotope to reside. For example, a position specific isotope signature in propane could refer to the position of the $^{13}C$ atom, which can be positioned either at the center of the compound (e.g., $CH_3$—$^{13}CH_2$—$CH_3$) or one of the terminal end positions (e.g., $^{13}CH_3$—$CH_2$—$CH_3$). Likewise, a position specific effect in propane could refer to the position of a D atom, which could be attached either to the central carbon (e.g., $CH_3$—$CDH$—$CH_3$) or to one (or more) of the terminal end position carbons (e.g., $CDH_2$—$CH_2$—$CH_3$). Similarly, for higher alkane molecules, a position specific isotope signature could refer to the position of the $^{13}C$ atom in one or more of the central positions (e.g., $CH_3$—$^{13}CH_2$—$CH_2$—$CH_2$—$CH_3$ or $CH_3$—$CH_2$—$^{13}CH_2$—$CH_2$—$CH_3$) or one or more of the terminal end positions (e.g., $^{13}CH_3$—$CH_2$—$CH_2$—$CH_2$—$CH_3$).

As used herein, "machine-readable medium" refers to a medium that participates in directly or indirectly providing signals, instructions and/or data. A machine-readable medium may take forms, including, but not limited to, non-volatile media (e.g. ROM, disk) and volatile media (RAM). Common forms of a machine-readable medium include, but are not limited to, a floppy disk, a flexible disk, a hard disk, a magnetic tape, other magnetic medium, a CD-ROM, other optical medium, punch cards, paper tape, other physical medium with patterns of holes, a RAM, a ROM, an EPROM, a FLASH-EPROM, or other memory chip or card, a memory stick, and other media from which a computer, a processor, or other electronic device can read.

As used herein, the term "region of interest" refers to an interval, compartment, or reservoir where hydrocarbons, non-hydrocarbon gases, and/or water may reside. Likewise, "regions of interest" may refer to multiple intervals, compartments, or reservoirs where hydrocarbons, non-hydrocarbon gases, and/or water may reside.

As used herein, the term "signatures" refers to the relative abundances, concentrations, and/or ratios of various elements, isotopes, and/or isotopologues of a given species. For example, a signature may be derived from the clumped isotopes or the position specific isotopes within a sample.

As used herein, the term "fingerprint" or "geochemical fingerprint" refers to a collection of geochemical signatures that are associated with a particular region of interest.

As used herein, the term "stochastic distribution" refers to a system where the stable isotopes in a given population of molecules are distributed randomly among all possible isotopologues in a given species.

As used herein, the term "thermogenic" refers to hydrocarbons generated from kerogen that is currently or has in the past been subjected to high temperatures and pressures.

Described herein are methods and techniques for using isotopic signatures, such as clumped isotope signatures and/or position specific isotope signatures, for determining characteristics of hydrocarbon sources. In particular, it has been found that isotopic signatures, such as clumped isotope signatures and/or position specific isotope signatures, of a hydrocarbon source are propagated to the isotopic signatures of hydrocarbon fluids that have been generated through maturation of the source and/or the secondary cracking of primary hydrocarbon products. That is, it has been found that clumped isotope signatures and/or position specific isotope signatures of the hydrocarbon source are carried through the maturation and secondary cracking processes, and are retained in the hydrocarbon fluids (such as hydrocarbon gases) that are ultimately expelled or seeped from the source. Therefore, the isotopic signatures of a sample of a volatile or non-volatile hydrocarbon fluid (such as a hydrocarbon gas) that has been produced or sampled from a seep or well can be used to determine characteristics about the source rock (e.g., age, maturity, type) from which the fluid was generated. Further, the isotopic signature can be integrated with other physical and geochemical information (such as pressure/volume/temperature properties, hydrocarbon composition, metal isotope composition, etc.) as well as with seismic information, or other information contained in basin models to determine additional characteristics of the source rock. This information can then be used to improve (i.e., derisk) hydrocarbon exploration and development operations and to infer the type and value of hydrocarbon products likely to be found.

Thus, the present methods and techniques take advantage of isotopologue geochemistry of hydrocarbon fluids and allow for the direct linking of a sample of a produced or seeped volatile or nonvolatile hydrocarbon fluid to a source material. The methods and techniques described herein generally comprise measuring a clumped isotope signature or a position specific isotope signature of a hydrocarbon species in a sample of hydrocarbon fluid to determine a measured or analytical signature. The measured/analytical signature can then be compared with or integrated into a modeled signature to determine characteristics of the source material (such as source maturity, hydrocarbon generation progress and rate, alteration, and/or mixing). The modeled signatures may be prepared from models that reflect different source compositions and isotopic structures, different kinetic processes, and/or different elements of a basin's history as described further herein. Thus, the modeled signature can be used to predict specific isotopic signatures of hydrocarbon fluids (such as hydrocarbon gases) from different starting source materials, and the closer the alignment between the modeled/predicted signature and the measured/analytical signature the more direct correlation can be made the sample and hydrocarbon source.

In particular, the measured clumped isotope signatures and measured position specific isotope signatures of one or more hydrocarbon species from a hydrocarbon fluid sample can be integrated with an understanding of the kinetic properties of the hydrocarbon species and kinetic properties of the hydrocarbon source organic matter to provide constraints on source facies. This is unanticipated, as it was previously believed that most geochemical information, apart from bulk isotopic signature (i.e., total amount of each type of isotope), that was directly related to the structure of the hydrocarbon source material was destroyed during hydrocarbon cracking processes. Therefore, using the methods and techniques described herein, it may be possible to distinguish hydrocarbon gases that come from different types of source materials (e.g., kerogen, bitumen, oil, larger gas molecules, biological materials from different organisms, or combinations thereof). Further, using the methods and techniques described herein it may be possible to distinguish between various types of hydrocarbon alteration (e.g., mixing and different biological or thermal processes) that have different kinetic isotope effects.

The methods and techniques described herein may also be used to characterize the source rock from which the hydrocarbon originated. For example, the modeling techniques described herein can be used to provide knowledge of how the isotopic signatures of hydrocarbons from differently sourced organic matter evolve during maturation. From this knowledge, it can be possible to determine the thermal maturity of the source rock from which the hydrocarbons derived.

Multiply substituted isotopologue geochemistry is based on the variation in the distribution of isotopes within a molecule that gives rise to molecules that are identical in their elemental compositions, but that may differ in the isotopic composition of individual atoms within that molecule. These species are called isotopologues. For example, there are three isotopologues of nitrogen ($^{14}N_2$, $^{15}N^{14}N$, and $^{15}N_2$). An isotopologue in which two or more rare isotopes are present is called a multiply-substituted isotopologue and when the rare isotopes are in close proximity (i.e., isotopic "clumps") the isotopologue is called a clumped isotope (e.g., $^{15}N_2$). Hydrocarbon isotopologues involve hydrocarbon compounds (e.g., those that contain carbon and hydrogen atoms) that have natural isotopes of $^{12}C$, $^{13}C$, $^{1}H$, or H (i.e., deuterium or "D"). $^{12}C$ represents about 98.93 mol % of the total carbon on Earth, while $^{13}C$ forms the remaining about 1.07 mol %. Similarly, the isotopic abundance of $^{1}H$ on earth is about 99.985 mol % while deuterium has an abundance of about 0.015 mol %. Common volatile hydrocarbons have large numbers of isotopologues, even when considering only the stable isotopes. For example, methane has 10 isotopologues, ethane has 36 isotopologues, and propane has 216 isotopologues. Common isotopologues of methane include, for example, $^{13}CH_3D$ or $^{12}CH_4$. In addition to the number of rare isotopes in an isotopologue, the distribution (i.e., position) of the rare isotopes in the molecule can also provide information about the molecule. For example, in a linear hydrocarbon with three or more carbon atoms (e.g., n-propane or n-butane), the rare isotope can take either a central or terminal (i.e., end of molecule) position. Similarly, rare isotopes of hydrogen can occupy different positions within the molecule. As the size of the hydrocarbon compound increases, the number of positions in which the rare isotopes can be situated increases. This effect is called the position specific isotope effect or isotopomer geochemistry.

The isotopic signature of a hydrocarbon species, such as the clumped isotope signature and the position specific isotope signature, is a function of (i) temperature-independent randomly populated processes (i.e., stochastic distribution) and (ii) other non-random mass fractioning processes. The stochastic distribution of any isotopologues can be determined from the bulk isotope signatures of the hydrocarbon species from which it derives. For example, the stochastic distribution of isotopologues of methane involve knowledge of the $^{13}C$ and D signatures of methane. Under equilibrium conditions, a non-stochastic distribution may result from thermodynamic differences between the different isotopologues. Under non-equilibrium conditions, the non-random processes may be temperature-time-dependent isotopic exchange reactions in some hydrocarbons. For example, the clumped isotope signature of methane can provide information about the equilibrium gas generation temperature. See e.g., Stopler et al. (2014), "Formation temperatures of thermogenic and biogenic methane", *Science*, Vol. 344, pp. 1500-1503.

Additional equilibrium or non-equilibrium kinetic isotope exchange processes may also influence the isotopic signatures of some hydrocarbon species. For example, these processes may include biodegradation, secondary thermal cracking of hydrocarbons, thermochemical oxidation/reduction reactions, mixing, and diffusion. These processes may differ in their relative magnitude of the impact on the isotopic signature, such as the clumped isotope signature and/or the position specific isotope signature. In addition to the magnitude of the effect on the signature, the time required for these processes to affect the signature may differ from hydrocarbon species to hydrocarbon species. Therefore, an understanding of the kinetic properties of different hydrocarbon species is also needed in order to model the isotopic effects of hydrocarbon fluids.

Modeling chemical transformations of molecular materials (such as hydrocarbon fluids) can be performed in various ways with various degrees of specificity. Typically, at a minimum, the species of interest (e.g., hydrocarbon species of interest) (or collections or subsets of the species of interest) need to be represented and those representations manipulated to express changes resulting from the transformations. The species can include reactants, products, and intermediates. A typical form of kinetic modeling is to represent the concentration of the species and any externally imposed conditions (e.g., temperature and pressure) with variables and the transformations between them as differential equations while also incorporating a variable for time. The variables could, optionally, be functions of position or be assigned to different phases. Starting from an initial state with specified concentrations, the differential equations are solved, to yield the concentrations at subsequent times.

One difficulty when modeling isotopologues of hydrocarbon species is that the number of isotopologue species that exist for any one hydrocarbon species and the number of differential equations that need to be solved can be very large. For example, ignoring deuterium substitution, a C40 normal alkane has 20 unique isotopologues containing one $^{13}C$ atom. For each of those, there are about 39 isotopologues containing two $^{13}C$ atoms, leading to (after accounting for non-unique symmetric species) 790 unique doubly-substituted isotopologues. For triple-substitution there are 30,020 unique species, and the number of isotopologue species continues to increase as the number of substitutions increases. Thus, the number of all possible isotopologues (counting only $^{13}C$ substitution and ignoring deuterium substitution) is extremely large. Thus, modeling a simple catabolic cracking mechanism for each of these C40 species includes 39 reactions leading to smaller species. A complete mechanistic model starting with only singly-substituted, doubly-substituted, and triply-substituted C40 molecules and tracking all resulting product species involves more than 100,000 isotopologue species and more than 1,000,000 reactions. Therefore, the level of complexity involved and the computing time needed to solve such equations can often prevent practical use of such models.

To overcome this difficulty, the inventors have found that, for the purposes of predicting the isotopic structures of smaller hydrocarbons produced during catabolic reaction pathways, it may not be necessary to take into account all 100,000+ isotopologue species described above. Rather, the model can account for a representative group of starting species that contain the relevant isotopic structures (e.g., sequences of $^{13}C$ and $^{12}C$ atoms in linear alkanes) with the correct ratios or proportions. For example, if the sequence $^{13}C^{12}C^{12}C^{13}C^{12}C$ exists, it may not be necessary to start with all possible species that contain the sequence in all possible locations. Instead, the model can create or include and track a representative sample of species containing the sequence and all other significant moieties. For example, if separate C40 species containing the sequence at starting positions 1, 5, 15, and 20 are included in a mechanism, then the smaller product molecules (e.g., the propane isotopologue $^{12}C^{13}C^{12}C$) may approximately encompass all of the molecules that would be generated by a mechanism that included all possible locations of that sequence. Thus, the species to be tracked in a mechanism could be generated by any scheme that produced the desired distribution of isotopic structures or moieties. Since most studies of isotopic structure assume a random or stochastic distribution of rare isotopes, a selection of species with a random distribution of $^{13}C$ atoms may be appropriate in most models.

In a kinetic scheme using representative species, choices have to be made as to which species are to be included and how many to include. A reaction network including these species must also be generated. An alternative is a scheme that instead tracks a large number of representative individual molecules generated such that all significant patterns of isotopic substitution are included. The inventors have surprisingly found that such a scheme can be made practically useful even though very large numbers of molecules are simulated. If the structure of the molecules is encoded, then the reactions that each molecule undergoes can be generated on-the-fly and the large number of reactions between all of the species (kinetic or network) need not be enumerated or programed. For example, in a simple first-order model for the cracking of linear alkanes (and ignoring H/D content), the structure of the molecules can be represented as character or number sequences or bit-strings. For example, the bit string 10010 Could correspond to the sequence of $^{12}C^{13}C^{12}C$. Such sequences of length N can represent linear alkanes containing N carbon atoms. Given this scheme, all alkanes generated in a cracking mechanism can be represented by simple character, number, or bit sequences of the same form. Tracking the state of such a kinetic system then involves storing in memory a large number of these sequences. The reactions occurring for a given species can be generated as needed from their structure. For example, a linear alkane of length N could crack at any of its N-1 bonds with a probability or rate that depends on molecular size, bond position, and the detailed isotopic structure of the atoms connected by that bond (leading to a primary kinetic isotope effect ("KIE")) and, optionally, depending on the identity of the other nearby atoms and/or molecules leading to a secondary KIE.

A kinetic Monte Carlo ("kMC") simulation of a reaction network comprises a set of starting molecules, such as those discussed above, and rules and probabilities for applying different reactions to those molecules at a sequence of 'steps'. The rules and probabilities for the reactions can be selected to give equivalent results as the set of reaction equations discussed above.

For example, the kMC rules and probabilities may be selected to use normalized relative rates as probabilities for selecting reactions. Thus, the faster a reaction, the more likely it is to be chosen in a given time step. In such an example, the kMC procedure may involve the following steps: (a) for every possible event i (where i≤N), calculate rates $r_i$ (if necessary); (b) calculate $r_t = \Sigma_1^j r_i$; (c) generate a random number from the uniform distribution: $u_1$: $0 \leq u_1 \leq 1$; (d) determine the smallest j such that $u_1 r_t < \Sigma_1^j r_i$; and (e) enact event j and update species. This procedure can thus be used to generate a stochastic simulation but ignores the calculation of time increments for each simulation step.

The rules for the kMC simulation may also be selected such that the steps are converted to time scales if desired. In such an example, the kMC simulation can yield similar information as the more typical reaction kinetics solution, and measure the amount of different species as a function of time or other reaction progress variable. Where in typical schemes, concentrations of species are tracked, in such a kMC simulation, the numbers of molecules of different types are tracked. Thus, the use of the kMC simulations offers the ability to eliminate the need to model the system through a direct representation of the complex reaction network that links all possible isotopologues in a system. Instead, the kMC allows one to model the system by simply storing a large number of individual molecules, complete with their isotopic structure, identify possible events for each molecule, and formulate the rules for generating the rates for each event from the structure of the individual molecules.

The starting state of the system that is being modeled can be simply specified by the user or can result from a previous simulation or a different type of simulation. For example, in some embodiments the isotopic structure of the starting molecules may be completely random or stochastic. In other embodiments, the isotopic structure of the starting molecules may be equilibrated with more thermodynamically stable moieties found with higher probability, such as probabilities that satisfy the Boltzmann distribution. In still other embodiments, it may be desirable to model particular natural phenomena such as a tendency for some plants to produce alkyl chains with a tendency for alternating $^{13}$C atoms down the alkyl chain or other isotopic structures resulting from equilibrium and kinetic processes.

When using a 'molecules' approach as opposed to a 'concentrations' approach, it may be preferable to use a different type of Monte Carlo scheme to produce the starting distribution. For example, an energy function can be defined that produces the energy, E, of any isotopologue based on the positions of the different isotopes. A standard Monte Carlo simulation (e.g., a Metropolis Monte Carlo ("MMC")) can be conducted which will tend to lower the free energy of the system by moving the different isotopes/atoms around, perhaps both within and between molecules. This procedure need not mimic physical reality, as the energy and other parameters, such as temperature, in the simulation can simply be chosen to give the desired results. For example, an alternation of $^{13}$C atoms along an alkyl chain can be produced by specifying an energy benefit (e.g., lowering) for $^{13}$C atoms occupying every-other position along the chain. Similarly, clumping of $^{13}$C atoms can be produced by specifying an energy benefit for adjacent $^{13}$C atoms. The simulation (such as the MMC) can then be run to steady state or stopped at any time to yield different distributions. For example, the simulation can be run to create distributions that reproduce experimental properties of interest such as bulk isotopic content, the degree of alteration, and/or a desired distribution of molecular sizes and types. Alternatively, a random or stochastic distribution may be specified and produced using a random number generator.

Multiple steps or preparatory procedures may be run in order to produce a starting distribution for the system being modeled by the kMC simulation. For example, an initially random distribution may be modified by one or more subsequent MMC simulations with different energy functions and other parameters. Some portion of the products of one kMC simulation, with prescribed conditions and parameters, can be used as the starting material for input to another kMC simulation with potentially different conditions and parameters.

Once the starting configuration is specified, the kMC simulation can begin and the procedure can be repeated until the desired conversion or time, or some other measure, is reached. At each step, probabilities for each contemplated reaction are calculated in such a way that they give relative rates equivalent to those in a differential equation approach. For example, if there is a kinetic isotope effect that slows the breaking of $^{13}$C$^{12}$C bonds relative to the breaking of $^{12}$C$^{12}$C bonds, then the probability of choosing a $^{13}$C$^{12}$C bond will be less than that of choosing a $^{12}$C$^{12}$C bond. Similarly, terminal bonds can be chosen with a higher or lower frequency than the same type of internal bond, according to the mechanism being modeled. Molecules that exist in higher numbers will be chosen more often than molecules that exist in lower numbers, thus incorporating the mass action effect in the simulated reaction rates. The probabilities or rates can be calculated from other models or methods, such as transition state theory coupled with quantum chemical calculations, or fit to the experimental results, or chosen to match measurements from field samples.

After the probabilities for selecting molecules and the reaction types (e.g., bond breaking) are calculated, a particular molecule and reaction are chosen with the help of random numbers. Then the reaction is implemented, the original molecule is destroyed and one or more new molecules are created. The procedure then repeats until the desired conversion rate, time step, or other previously determined measure is reached.

As described above, a kMC simulation may be used to model the thermal cracking of linear alkanes into smaller alkanes. While real thermal hydrocarbon cracking occurs through free radical reactions with β-elimination, H-transfer, recombination, etc., the final gaseous products of such reactions are mostly small alkanes whose isotopic structures can be easily measured and analyzed.

In a kMC simulation for use herein, the events or reactions of interest may be characterized by Equation 1:

$$C_n \rightarrow C_m + C_{n-m} \qquad \text{(Equation 1)}$$

where $C_n$ is a linear alkane molecule containing n carbon atoms. Each event/reaction breaks a C—C bond in $C_n$ and the fragments $C_m$ and $C_{n-m}$ inherit the unchanged isotopic structure of their respective portions of the original $C_n$ molecule. Equation 1 focuses on the carbon isotopic structure, ignoring H/D substitutions, and assumes that missing H atoms required to saturate the fragments are supplied by other hydrocarbon molecules or elsewhere in the environment.

The kinetic model requires rate parameters for all of the included events or transformations. For example, for bond-cracking alkanes, the rates are known to depend on the size of the molecules, the position of the bond within the molecule, and/or any kinetic isotope effects. Thus, a rate constant or rate parameter, such as an isothermal rate constant (k), the Arrhenius activation energy ($E_a$), or an Arrhenius pre-factor (A) for a particular event, can be characterized by Equation 2:

$$k = k(n, p, i) \qquad \text{(Equation 2)}$$

where n refers to the length (or carbon number) of the molecule, p refers to the bond position (i.e., the number of bonds away from the end of the molecule, where p=0 is the terminal bond), and i refers to the isotopic identity of the atoms connected by the bond (e.g., i=0 for $^{12}C^{12}C$ bonds, i=1 for $^{12}C^{13}C$ bonds, and i=2 for $^{13}C^{12}C$ bonds).

As an example, a straight-forward form of the relationship in Equation 2 may be to simply assign separate rate constants for each bond on each type of molecule with each isotopic form, where $k(n, p, i)=k_{npi}$, with each $k_{npi}$ being separately assigned or fit to data. This straight-forward form may be difficult to model due to the large number of different species and reactions in the systems contemplated herein. However, simplifying assumptions may be made as one would expect the parameters for bonds in similar environments to have similar values and for the effects of isotopic substitution, molecular size, and bond position to be at least somewhat independent. Therefore, functions for each of these effects may be created, such as in Equation 3:

$$k_{npi}=f(n)g(p,n)h(i,p,n) \quad \text{(Equation 3)}$$

where $f$ incorporates the effects of molecular size, g incorporates the effects of bond position and mixed size/position effects, and h incorporates the effects of isotopic substitution and any further mixed effects.

As an example, $k_{npi}$ may be determined as follows. While not true in general, for simplicity, one can assume that there is no position dependence for bond breaking, and, thus, that $g(p,n)=1.0$. Similarly, the basis for kinetic isotope effects may be assigned as 1.0 for $^{12}C^{12}C$ bonds, and thus, $h(n,p,i)=1.0$. The function $f$ may be determined by assuming that in general, cracking rates for alkanes increase as molecular size increases. Thus, for alkanes having more than 3 Carbon atoms, the following Equation 4 may be used to determine the function $f$:

$$f(n>3)=a+b(n-4) \quad \text{(Equation 4)}$$

where a and b may be chosen based on the base rate in the system of interest. Thus, the $^{12}C^{12}C$ bond breaking rate for butane is $\alpha$, and the rate constant grows by b for every additional C atom in the molecule. For example, if the typical bond cracking rate for hexane is the base rate in the system, a and b may be chosen that bonds in hexane give $f=1.0$ and in such as case a=0.43116 and b=0.28442.

In this example, the second or higher-order kinetic isotope effects can be ignored, and constant multiplies may be used to give the rates of $^{12}C^{13}C$ and $^{13}C^{13}C$ bond braking. A uniform 3% kinetic isotope effect may also be assumed, and a "clumped isotope" KIE may be the square of the single substitution KIE. For example, $h(n,p,1)=0.97$ and $h(n,p,2)=0.97^2=0.941$. In such a manner the KIE effects are kept independent of molecular size or bond position. However, if more information on the clumped isotope KIE was available, it could be used to modify the h function.

The cracking reactions of ethane and propane can be anticipated to be anomalous, and, thus, the cracking rates of ethane and propane can be set idiosyncratically. For example, for isothermal rate constants k, for $^{12}C^{12}C$ bond, can be set as: $f$(ethane, $^{12}C^{12}C$ bonds)=$f(200)$=0.02 and $f$(propane, $^{12}C^{12}C$ bonds)=$f(300)$=0.20.

In this example, there are no position dependent for these species (g=1) since they only have one type of bond. Thus, the cracking rate for $^{12}C^{13}C$ bonds in propane may be: $k(300)=f(3)*g(3,0)*h(3,0,1)=0.20*1*0.97$. In such a manner, the $k_{npi}$ may be determined. In this example, the model functions were chosen with a focus on simplicity. However, more accurate functional forms and parameters could be developed to more closely match experimental results and to model increased complexity systems that include intermediate species and reversibility.

There are different ways of running simulations, including kMC simulations, which are known in the art and which may lead to efficiencies in running any particular kinetic scheme. For example, various data structures may be used to represent the molecules in the system. As described above, an n-alkane's size and $^{13}C$ structure may be represented by a sequence of bits, characters, or numbers. For example, hexane with a single terminal-substituted methyl group can be represented by "100000" (or equivalently, "000001") and the two forms of methane may be represented as "0" and "1" for $^{12}CH_4$ and $^{13}CH_4$, respectively. In the "molecules" approach, each explicitly represented molecule requires computer memory to hold this structure. This has the advantage in that reactions don't have to be represented directly by equations involving multiple species and can be implemented by splitting the molecule and having fragments that inherit the isotopes of the parent (e.g., 100000→100+000). A hybrid approach may also be used, where molecules are explicitly represented with sequences, but a few common ones are represented with a simple count of the number of those molecules. For example, at the end of a long simulation, most of the atoms are contained in methane molecules for which there are only two types and which don't participate in any reactions and therefore, do not need to be included in the list of possible events. As such, the methane molecules may be held in an array such that methane implicit[0] holds the number of $^{12}CH_4$ molecules and methane implicit[1] holds the number of $^{13}CH_4$ molecules.

Since the natural abundance of $^{13}C$ is approximately 0.01, many or most moderately sized alkanes in unenriched systems contain no $^{13}C$ atoms. Thus, in the above approach, they would be represented by sequences of 0 with length equal to the number of C atoms in the molecule. The total event rate for each of these molecules is just $(n-1)*k(n00)=(n-1)*k_{1212}$ and never changes. They can also be represented by an array, such that mols_implict[n] holds the number of each unsubstituted alkanes of length n:n≥2. When unsubstituted alkanes are cleaved, the reaction is implemented by the element of this array for n being decremented and those for m and n−m being incremented. As such, the explicitly represented molecules are held in an array which contains the bit sequences described above and which has an element for each explicit molecule.

When independent simulations are used and combined, the independent simulations can be run sequentially or in parallel on different computer processors, or both sequentially and in parallel, and the results automatically combined with software. This may be useful even when modeling only a single type of starting molecule, such as a C20 alkane. Some product species of interest, such as a gas molecule with a very specific isotopic structure, may be present in the products at only very low levels. In order to gather enough product species to have usable statistics regarding their population, the kinetic processes of a large number of starting molecules must be simulated. The required number may exceed the memory or other capabilities of a given computer. Running multiple simulations and combining the results can provide the necessary numbers and lead to useful statistical properties. For example, it may be most efficient to run simulations of 100,000 starting molecules, but $10^{11}$ starting molecules may be required to achieve useful results for a product species that is only produced for 1 out of $10^8$ starting molecules. In this case, 100,000 separate simulations may be run (with appropriately randomized starting conditions), and perhaps 1000 of them sequentially on each of 1000 different processors or in any other useful combination.

This process can be repeated using as many cores/processors as available or necessary in order to achieve the desired statistics for the rarest species of interest. For example, if only about $1/10^6$ propane molecules are triply-$^{13}$C-substituted and only approximately 1000 propane molecules are present at some stage of a typical simulation, only about $10^{-3}$ such triply-substituted propane molecules will exist in each simulation on average at that stage. In order to sufficiently characterize the number of those molecules at that stage, at least $10^5$ or $10^6$ simulations may need to be performed. It is interest in these rare species and the consequent number of simulations necessary to accumulate precise statistics that sets the cpu-time requirements for studying detailed isotopic structures of molecules. Thus, large-scale high performance computing may be necessary.

The kMC simulations can be run in various ways to achieve the same or similar objectives. For example, for any portions of kinetic networks that do not interact, the simulations can be run separately or independently. For example, in first-order reaction schemes where biomolecular reactions do not occur, the rates and probabilities depend only on the number of each species present in the simulation. Different molecules and isotopologues can be run separately and the results combined, according to the desired distribution of starting molecules, to produce the resulting species and their isotopic and molecular signatures.

There are other variations useable within kMC simulations, such as different methods for calculating the probabilities and choosing individual reaction steps and different methods for creating or implementing the reaction scheme, including automated methods, and all such methods are contemplated herein.

Further, for purposes of comparing the results of the kMC simulation to measured compositional and isotopic properties of natural hydrocarbon fluids, it may be useful or necessary to choose only a subset of the molecules produced from the simulations. For example, if a physical fluid is thought to contain only gas molecules produced from early stages of transformation of the source material, then molecules from only the early stages of the modeled kinetic process are considered as "results" to be compared with the measurements. Different portions of the modeled product molecules could be compared to the measurements in order to select between different candidate models for the source and/or process of maturation. Similarly, if a seal or trap structure is developed only sometime after source maturation begins, then a later portion of the produced molecules from the simulation should be compared to measurements of a sample reservoir or seep fluid.

As an example the present methods and techniques may utilize a kMC simulation as follows. First an initial population of molecules is created or selected. The initial population of molecules may be created by selecting a molecular length and randomly inserting $^{13}$C atoms into this population until the desired average $^{13}$C content is achieved. For example, this can be done until a random or stochastic population of $^{12}C^{12}C$, $^{12}C^{13}C$, and $^{13}C^{13}C$ bonds and a stochastic population of all larger fragments is achieved. When there is a desire to determine a sensitivity of the results to different starting distributions of $^{13}$C is desired, a Metropolis Monte Carlo simulation may be applied to the initial stochastic populations of molecules as described above. For example, to create an initial population where $^{13}$C atoms tend to be "clumped", a MMC simulation may be conducted where a negative energy penalty, E=−1, may be applied whenever $^{13}$C atoms are adjacent to one another. The temperature, kT, may then be varied until the desired level of clumping is achieved in the MMC simulation of a specified number of steps. Conversely, to create an initial population where $^{13}$C atoms to avoid one another, a positive energy penalty, E=+1, may be used. Thus, the MMC may operate to produce random swaps of atoms in different positions on the same molecule or random swaps of atoms in different molecules to achieve the desired distributions.

Once the initial molecule populations are determined, the kMC simulation is conducted on the initial molecule population. To conduct the kMC simulation it is desired to determine the possible events, and calculate the rate or frequency of such events. The molecules on which to enact the events are then chosen, for example by a random number generator, and the event is carried out on the molecules according to the rate/frequency function. The resulting molecule species are then updated, and the process may be repeated until all desired events have taken place.

In some embodiments of the kMC simulations time may be ignored, and rather quantities of interest (such as functions of conversion or other variables) may be used to determine when the reaction has completed. For example, the conversion percent is related to the reaction progress and the fraction of reactant remaining. However, in some embodiments, it may be desirable to add a time function for the steps of the kMC simulation. In such embodiments, the time function may be related to the Poisson nature of the events.

The present methods and techniques may be further understood with reference to FIGS. 1 to 7, which are described further below. The present methods and techniques described herein may also be better appreciated with reference to flow diagrams (such as those in FIGS. 2 to 4). While for purposes of simplicity of explanation, the illustrated methodologies may be shown and described as a series of blocks in FIGS. 2 to 4, it is to be appreciated that the methodologies are not limited by the order of the blocks, as some blocks can occur in different orders and/or concurrently with other blocks from that shown and described. Moreover, less than all the illustrated blocks may be required to implement various embodiments of an example methodology. Blocks may be combined or separated into multiple components. Furthermore, additional and/or alternative methodologies can employ additional blocks not shown herein. While the figures illustrate various actions occurring serially, it is to be appreciated that various actions could occur in series, substantially in parallel, and/or at substantially different points in time.

FIG. 1 is a side elevational diagram 100 of components of a hydrocarbon system in a subsurface region. In diagram 100, Components and events in a hydrocarbon system are provided for a subsurface region 102, which may be at least partially below a body of water 104. The processes of a hydrocarbon system involve generation, migration, trap formation, accumulation or leakage to a seep, and/or preservation. The elements (or components) of the hydrocarbon system include various portions of a formation, such as source rocks 106, reservoir rocks 108, and seal rocks 128. Hydrocarbon systems analysis may involve determining source presence, source maturation, trap presence, migration pathways, reservoir presence, trap seal presence, and timing. The hydrocarbons may be produced through a wellbore 126.

As an example, the hydrocarbon system process may involve various steps to form current hydrocarbon locations. First, hydrocarbons are generated, which occurs in source rock 106. Then, the hydrocarbons migrate from the source rock 106 through faults and fractures, such as fracture 111, as shown by arrows 112, 114, 116, and 118. Hydrocarbons accumulate in a reservoir 110. Accumulation of hydrocarbons can only occur if a trapping structure is present at the same time or before hydrocarbons migrate through the reservoir rock 108 if an adequate seal rock 128 is in place. Hydrocarbons can be stored in an accumulation 110 and preserved, as shown by seal rocks 128 or may be seeped by a fracture through a fault line 120. If limited by subsurface geology, the hydrocarbons may be trapped in hydrocarbon accumulations 110, such as a gas reservoir and/or an oil/gas reservoir. Hydrocarbons may bubble and seep 122 from the subsea surface 132 into the body of water 104, via a fault 120, and form an oil slick 124 on the surface of the body of water 104.

Figure 2:
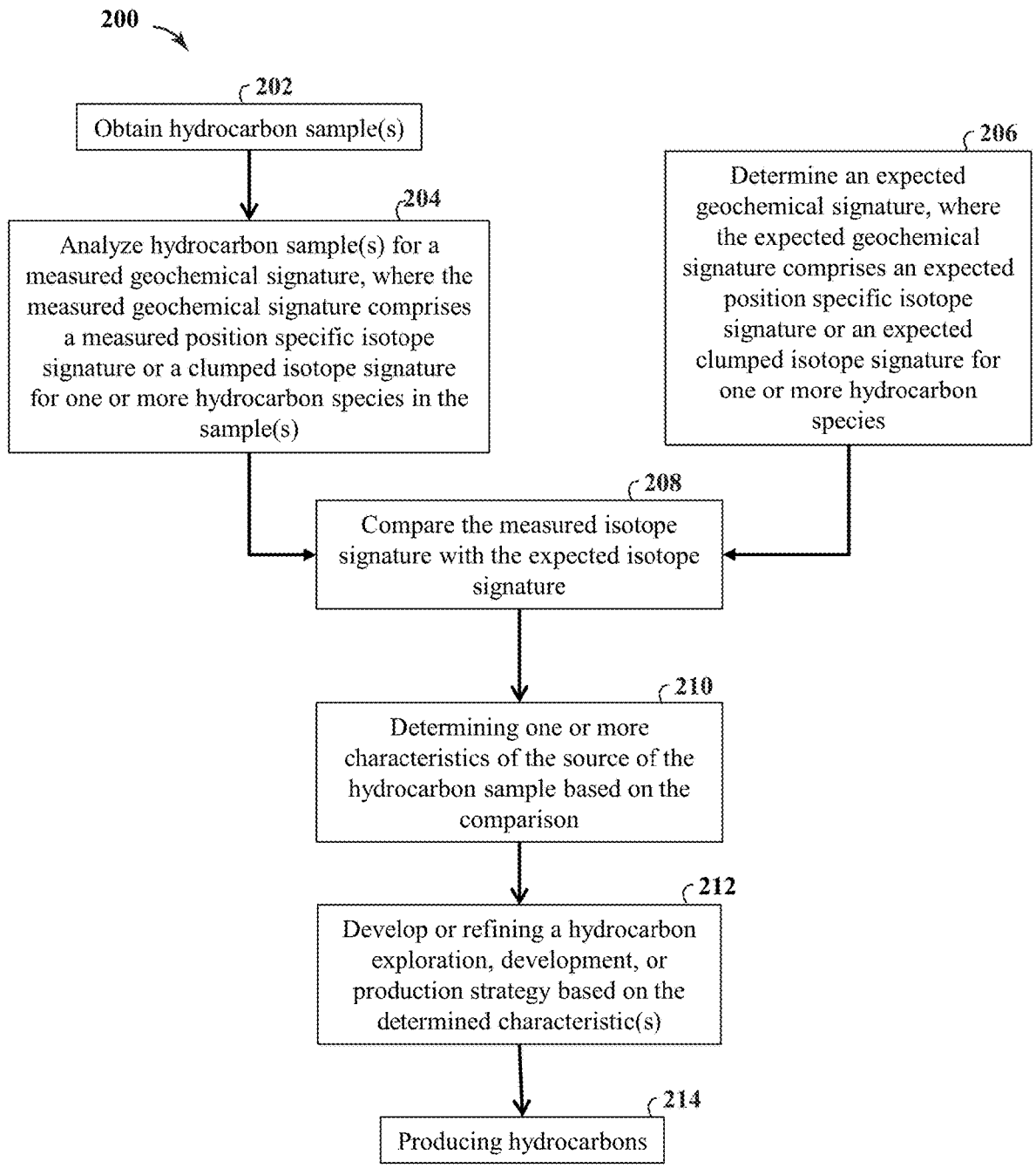
FIG. 2 is a flow diagram of an exemplary methodology in accordance with the present techniques.

FIG. 2 is a flow diagram 200 of an exemplary method in accordance with embodiments of the present techniques. The flow diagram 200 includes the acquisition of a sample, analysis of the sample to determine a measured isotopic signature of the sample, a comparison of a measured isotopic signature with an expected isotopic signature, and a determination of one or more characteristics of the source of the hydrocarbon sample based on the comparison.

At block 202 a sample of hydrocarbon(s) is obtained. The sample may be from a source rock, from a reservoir, from a seep, from drilling fluids, and/or from mud gases. The sample can be a sample of hydrocarbon fluids in the form of oil and/or gas obtained from the subsurface, at a surface location, such as seep, and may be in the form of free oil and/or gas, as solid hydrocarbons, or may be trapped within a rock sample. For example, the sample may be a reservoir sample and may be from a single phase gas in the reservoir or a flashed gas from an oil/condensate. As another example, the sample may be a seep sample and may be from a natural or anthropogenic sample. Reservoir samples or other samples taken from a well may be obtained downhole or at an available separator that is topside. In preferred embodiments, the sample may be a hydrocarbon fluid sample and may comprise hydrocarbons and associated gases (e.g., carbon dioxide). For example, the hydrocarbon fluid sample may comprise hydrocarbons, such as at least one of methane, ethane, propane, butane, pentane, hexane, heptane, octane, nonane, decane, and combinations thereof.

At block 204 the sample is analyzed for a geochemical signature. In preferred embodiments, the sample is analyzed for one or more isotopic signatures of one or more hydrocarbon species of interest, which may comprise an isotopic signature such as a measured clumped isotope signature or a measured position specific isotope signature. The hydrocarbon species of interest may be any volatile or non-volatile hydrocarbon species contained within the sample. For example, the hydrocarbon species of interest may be an alkane, alkene, aromatic, polar, or alsphaltene compound. Additionally, the hydrocarbon species of interest may also contain other substituent molecules in addition to carbon and hydrogen. The clumped isotope signature or position specific isotope signature may be an indication of whether any of the substituent molecules are rare isotopes.

In some embodiments, the isotope signature is a position specific isotope signature. For example, the position specific isotope signature may provide an indication of the ratio, relative proportion, or amount of $^{13}C$ and/or D in the hydrocarbon species of interest. For example, in some embodiments the hydrocarbon species of interest may be a linear alkane or linear alkene and the position specific isotope signature of interest may provide an indication of a ratio, relative proportion, or difference between the amount of $^{13}C$ atoms at central positions in the hydrocarbon species to the amount of $^{13}C$ atoms at terminal positions in the hydrocarbon species of interest. For example, the sample may be analyzed to determine a position specific isotope signature of propane. As an example, the sample may be analyzed to determine the relative amounts or ratio of propane molecules in the sample that have a $^{13}C$ atom in the center position to those that have a $^{13}C$ atom at a terminal (i.e., end) position.

In some embodiments, the isotopic signature is a clumped isotope signature. For example, a clumped isotope signature may provide an indication of the ratio, relative proportion, or amount of hydrocarbon molecules that contain two $^{13}C$ atoms next to each other in the chain, or contain two D atoms on the same C atom, or that contain a D atom off of two adjacent carbon atoms in the chain. For example, in some embodiments, the hydrocarbon species of interest may be a linear alkane or linear alkene and the clumped isotope signature of interest may provide an indication of the ratio, relative proportion, or difference between the amount of a hydrocarbon species that contain a clumped isotope and the amount of the hydrocarbon species that do not contain a clumped isotope. For example, the sample may be analyzed to determine a clumped isotope signature of ethane, and may be analyzed to determine the ratio or relative proportion of ethane molecules that have two rare isotopes (e.g., $^{13}CH_3^{13}CH_3$) to those ethane molecules that contain only one rare isotope or no rare isotopes.

The isotopic signature of a hydrocarbon species, such as the clumped isotope signature and/or the position specific isotopic signature, can be measured by a variety of techniques known in the art. For example, the isotopic signature may be measured through mass spectrometry, NMR, pyrolysis GC/MS, or other decomposition techniques. For example, Gao et al. (2016), "Determination of position-specific carbon isotope ratios in propane from hydrocarbon gas mixtures", *Chemical Geology*, Vol. 435, p. 1-9, describes a process of measuring propane position-specific carbon isotope ratios in hydrocarbon gas mixtures where the process includes separating/enriching the propane from the gas mixture and enzymatic and chemical reactions to convert the propane to acetic acid. As another example, Gilbert et al. (2016), "Measurement of position-specific $^{13}C$ isotopic composition of propane at the nanomole level", *Geochimica et Cosmochimica Acta*, Vol. 177, pp. 205-216, describes a process of measuring propane position-specific carbon isotope distributions using on-line pyrolysis of propane followed by analysis of carbon isotope ratios of the pyrolytic products methane, ethylene, and ethane. As yet another example, Piasecki et al. (2016), "Analysis of the site-specific carbon isotope composition of propane by gas source isotope ratio mass spectrometer", *Geochimica et Cosmochimica Acta*, Vol. 188, pp. 58-72, describes site-specific isotope ratio measurements using high-resolution isotope ratio mass spectrometry.

In addition to measuring a clumped isotope signature and/or position specific isotope signatures, the sample may be analyzed for other geochemical signatures. For example, the sample may be analyzed to determine a bulk isotope signature (e.g., total amount of $^{13}C$ or D in the sample), bulk metal signature (e.g., Vanadium and/or Nickel contents), and/or isotopic signature of non-hydrocarbon species in the sample (e.g., metal isotope signature or noble gas isotope signature). The sample may also be analyzed to determine other physical parameters, such as freezing point or boiling point. Additional, the sample may be analyzed to determine a biological signature, such as a signature indicating the community structure of microorganisms (such as bacteria and archaea) that are present in the sample or a signature indicating the community function of microorganisms that are present in the sample.

At block 206 an expected geochemical signature is determined. For example, an expected clumped isotope signature and/or position specific isotope signature for one or more hydrocarbon species in the sample may be determined based on different starting materials. The expected geochemical signature may be determined using the modeling methods described above, such as the kinetic Monte Carlo methods, or the methods described with further reference to FIG. 3 or 4 below.

For example, if the hydrocarbon species of interest is propane, an expected signature of the relative amounts or ratio of $^{13}C$ at the terminal (i.e., end or methyl position) and central (i.e., methylene position) positions can be determined based on an analysis of the kinetics of the expected source material. That is, the relative amounts, or the difference, of $^{13}C$ found at these two sites has been found to reflect important characteristics of the hydrocarbon source form which the propane was generated. The length of the alkyl chains present in the source material reflects the type of source and has a direct influence on the central vs. terminal position of the $^{13}C$ found in the propane. Thus, it is possible to infer or constrain the type of the source by measuring this signature and comparing it to an expected (or modeled) signature. Similarly, if the $^{13}C$ position specific isotope signature of two sources differ, this can be determined from the structure of the generated propane or other volatiles and non-volatile hydrocarbons and the nature of the kinetic processes producing the hydrocarbons of interest.

For example, some biological processes which generate source materials produce molecules with $^{13}C$ atom fractions which tend to vary with position in different ways depending on the producing organism. For example, alkyl lipids tend to feature alternating sites along a chain with more or less $^{13}C$, whereas isoprenoid lipids tend to feature two types of $^{13}C$ distribution patterns. This difference is carried through to the resulting propane molecules and can be used to indicate the type of source organism (e.g., eukaryotes, archaea, and/or bacteria, or specific subgroups within these domains).

The history of the isotopic structure of relevant molecules from an initial source material all the way to the generated gas can be simulated and modeled to create the expected geochemical signature of a sample. For example "kinetic Monte Carlo" ("kMC") simulations of various hydrocarbon starting materials can be conducted. The starting materials used in the simulation can be varied to reflect different molecular compositions and initial isotope specific structures (such as with or without isotope clumping, and varying the positions of rare isotopes within the molecules). Subsequent cracking reactions can then be modeled and the multiply-substituted and/or site-specific structure of the product molecules tracked. Therefore, by conducting simulations with source materials having different molecular characteristics and different site-specific structures, a correlation between the hydrocarbon source and resulting gas isotopic structures can be formed.

Figure 5:
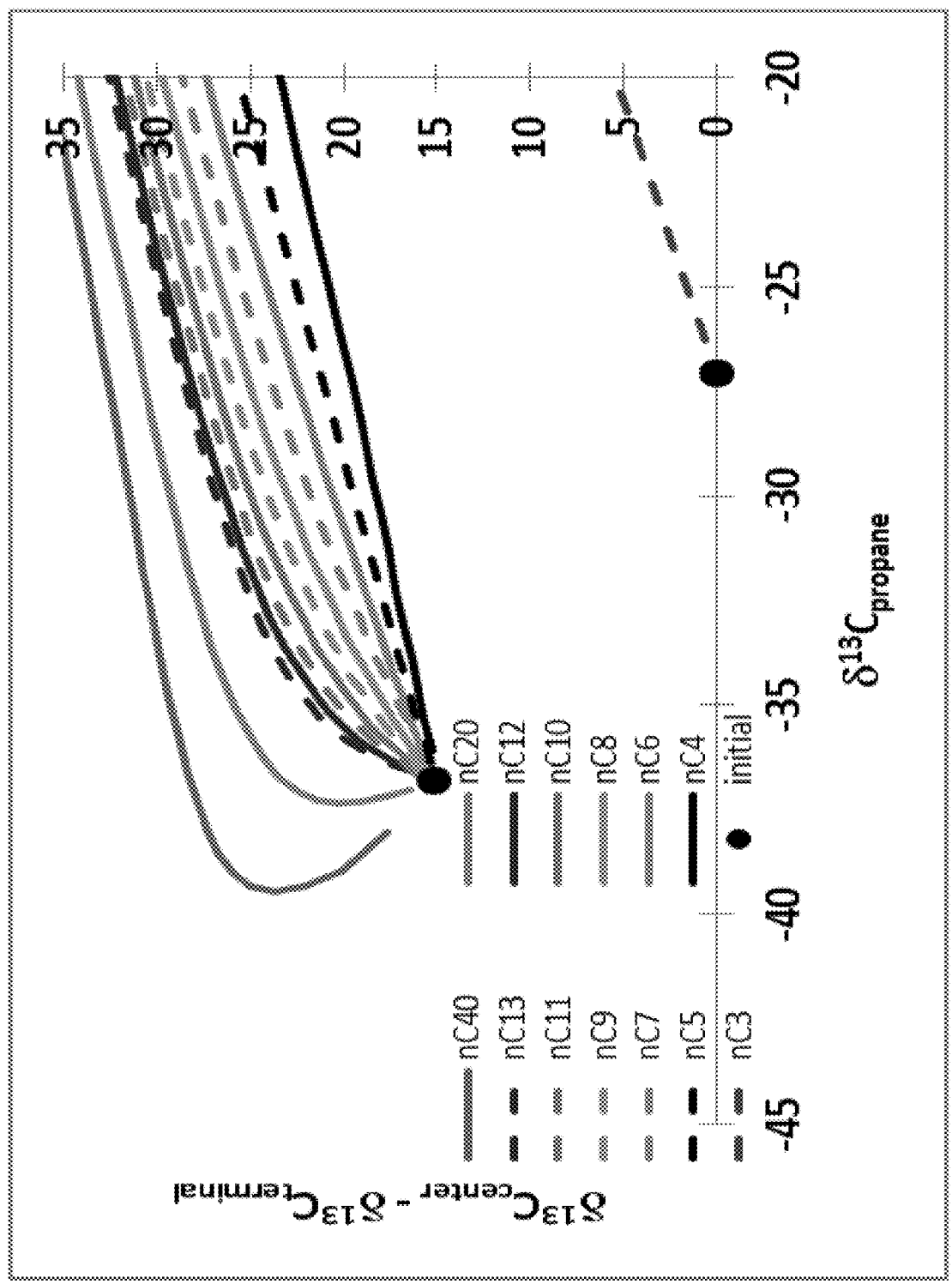
FIG. 5 is an exemplary plot of the results of a kinetic Monte Carlo simulation showing the difference in the $^{13}$C content of the center and terminal carbon positions of propane for different starting alkane chain lengths.
Figure 6:
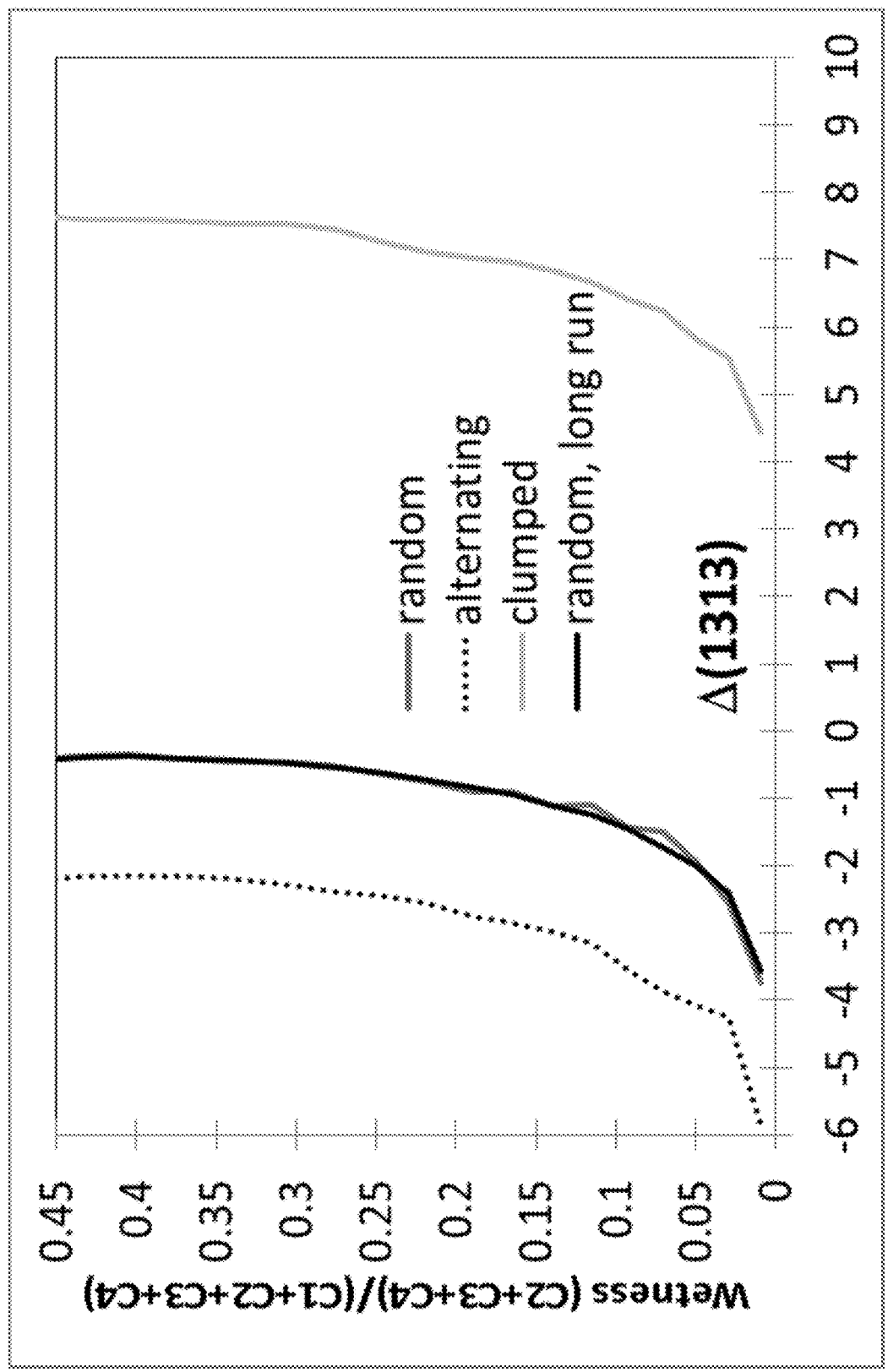
FIG. 6 is an exemplary plot of the results of a kinetic Monte Carlo simulation showing the relationship between thermal maturity (as indicated by wetness) and $^{13}$C distribution for cases starting from sources that are random, alternating, or clumped.

As an example, FIGS. 5 and 6 illustrate expected isotopic signatures that may be produced for various starting materials at block 206 of FIG. 2. That is, FIG. 5 provides an example of the results of kMC simulations that can be performed using alkane starting materials that had from 3 to 40 carbon atoms. FIG. 5 plots the position specific isotope signature (i.e., $^{13}C_{center}$ minus $^{13}C_{terminal}$) of the resulting propane molecules from each starting material versus the overall (or average) $^{13}C$ content of the propane molecules.

Each source alkane used in the simulation started with a random or stochastic distribution of the $^{13}C$ atoms, and the kinetic cracking of the starting materials was solved with the kMC simulation. As seen in FIG. 5, the initial chain length N>3 had an initial bulk $^{13}C$ signature of about −37‰. When the starting alkane was propane (i.e., N=3), the initial gas signature started at about −28‰ (which is the assumed bulk signature of the source in all of the simulations). For simulations starting from propane, the results shown are for the propane which is residual to the cracking process.

FIG. 6 provides another example of simulations which illustrate the effect of different levels of $^{13}C$ alternation or clumping in the source material. In particular FIG. 6, plots an indication of the gas wetness (i.e., a measure of the ratio of C2-C4 hydrocarbons to C1-C4 hydrocarbons in a sample which is inversely related to maturity or extent of conversion) versus the $^{13}C^{13}C$ clumping signature of the produced ethane molecules. The simulations all started from pure C20 alkanes and used the same level of $^{13}C$ in the starting source material (about −27‰), but the starting source materials had different detailed isotopic structures: stochastically random $^{13}C$ positioning, alternating $^{13}C$ positioning (with about 20‰ bias in alternating positions), or clumped $^{13}C$ positioning in the starting alkane chain. By running the kMC simulations, an indication of the $^{13}C$ clumped isotope signature of the resulting ethane molecules was obtained, and as seen in FIG. 6 the resulting ethane signature varied based on the starting materials. In particular in FIG. 6, it can be seen that the clumped signature carried through in that for the simulation where the $^{13}C$ in the starting material was clumped together, the resulting ethane also had a clumped signature.

The simulations used to determine the expected geochemical signature at in FIGS. 5 and 6 model the thermal cracking of various alkane starting materials to form hydrocarbons. The models use various rate constants to account for temperature dependence, level of cracking, and maturity of the starting and ending materials. However, the models can also be adapted and different rate constants can be used to constrain the model and mimic various other geological and biological processes such as biodegradation, mixing, hoteling, etc.

Further, while the simulations in FIGS. 5 and 6 were described using alkane starting materials, the simulations and models could be adapted to use different starting materials such as alkenes or cyclic hydrocarbons. For example, the models could be adapted to look at the isotopic signatures that result when a rare isotope is present on an alkyl substituent of an aromatic compounds.

Further, while the above simulations were described using kinetic Monte Carlo methods to solve for the resulting hydrocarbons, other methods could also be used. For example, other kinetic and/or equilibrium models that can track the transfer of isotopes among different bonding sites may be uses so long as the model allows the tracking/observation of site-specific effects. Additionally, the models may be adapted to have additional algorithms to predict the probability of a certain isotope to be in any given position of a molecule outside of the kMC probabilistic approach.

Returning to FIG. 2, at block 208 a comparison of the measured signature and the expected signature is made. For example, the measured signature may be compared to an expected signature (such as one or more of the expected signatures illustrated in FIGS. 5 and 6). Another example may be to compare the measured signature to data from empirical observations or other data sets. For example, one may compare the measured signature with databases of samples previously analyzed from different locations that have experienced different alteration processes and at different levels of alteration.

Alteration of gases can be observed in physical parameters such as bulk gas composition and ratios, as well as in other properties such as gas-to-oil ratios, presence of non-hydrocarbon gases (e.g., $CO_2$ or $H_2S$), API of oils, weight percent of sulfur, etc. These parameters can be measured in the hydrocarbon sample and integrated with the measured and/or expected isotopic signatures to refine and/or calibrate the expected signature.

At block 210 one or more characteristics of the source of the hydrocarbon sample is determined. For example, referring again to FIG. 6, if the comparison illustrates that the measured signature has retained a clumped pattern, one may infer that the source facies also possessed a clumped $^{13}C$ signature. This can then be used to correlate the source to different archaea or bacteria which affect the alternation vs. random positioning of $^{13}C$ in their lipid by-products which are used as a source material.

Returning to FIG. 2, at block 212 hydrocarbon exploration, development, and/or production strategies may be developed or refined based on the determined characteristic(s). For example, the results of the methods and techniques described with reference to FIG. 2 can be integrated with conventional exploration or prospect assessment techniques to confirm or de-risk the presence and/or location of a hydrocarbon accumulation and to assess potential migration pathways from the source rock to the seep. Such technologies may include reflection seismic imaging, high resolution seismic imaging, acoustic, basin modeling, and/or probabilistic or statistical assessments. By integrating these technologies, various characteristics of the accumulation may be estimated, such as hydrocarbon volume, hydrocarbon type (e.g., oil vs. gas), and the like.

Once a hydrocarbon accumulation has been identified and located, the hydrocarbons therein may be extracted or otherwise produced at block 214 using known principles of hydrocarbon operations. Producing hydrocarbons may include operations, such as modeling the location to drill a well, drilling a well, building surface facilities to produce the hydrocarbons, along with other operations conducted in and/or associated with the well after the well is completed. Accordingly, producing hydrocarbons may include hydrocarbon extraction, along with injection of gas or liquid for increasing drive pressure, mobilizing the hydrocarbons, hydraulic fracturing of a wellbore to promote increased flow, well servicing, well logging, and other well and wellbore treatments.

The methods and techniques described herein use geochemical signatures, such as clumped isotope signatures and/or position specific isotope signatures, combined with models linking detailed descriptions of source isotopic structures to gas isotopic structures, to constrain key elements of the hydrocarbon source using only samples of natural gas sampled from seeps or wells. Such information can aid in the determination of type of hydrocarbon resource presence (e.g., oil vs. gas) and in de-risking a play in a hydrocarbon system. In particular the present methods and techniques incorporate information about the entirety of the maturity process, from generation of the hydrocarbon through secondary cracking of the hydrocarbon, to aid in the determination of source facies and identification of source material (e.g., marine, terrestrial). Furthermore, the present methods and techniques can aid in the identification of whether a sample of hydrocarbon gas was produced from a particular source of hydrocarbon source oil.

The present methods and techniques may also be used to de-risk various hydrocarbon plays. For example, the seismic data for a prospective hydrocarbon reservoir may indicate that there are several potential hydrocarbon sources. The kMC techniques described herein may be used to model an expected geochemical signatures, such as clumped isotope signatures and/or position specific isotope signatures, for the different potential hydrocarbon sources. These potential signatures can then be compared against a measured signature of a sample from the reservoir to determine which potential source the sample was obtained from. This can then provide guidance as to where to drill wells in the reservoir in order to reach hydrocarbons from the source of interest. This can be particularly useful when there are multiple potential stacked sources which have different levels of maturity, as once the most likely source is identified (by comparing the predicted signature with the measured signatures), the user can update the basin model to emphasize which source is charging the system (which can then provide further information about other fluid properties in the system).

Figure 3:
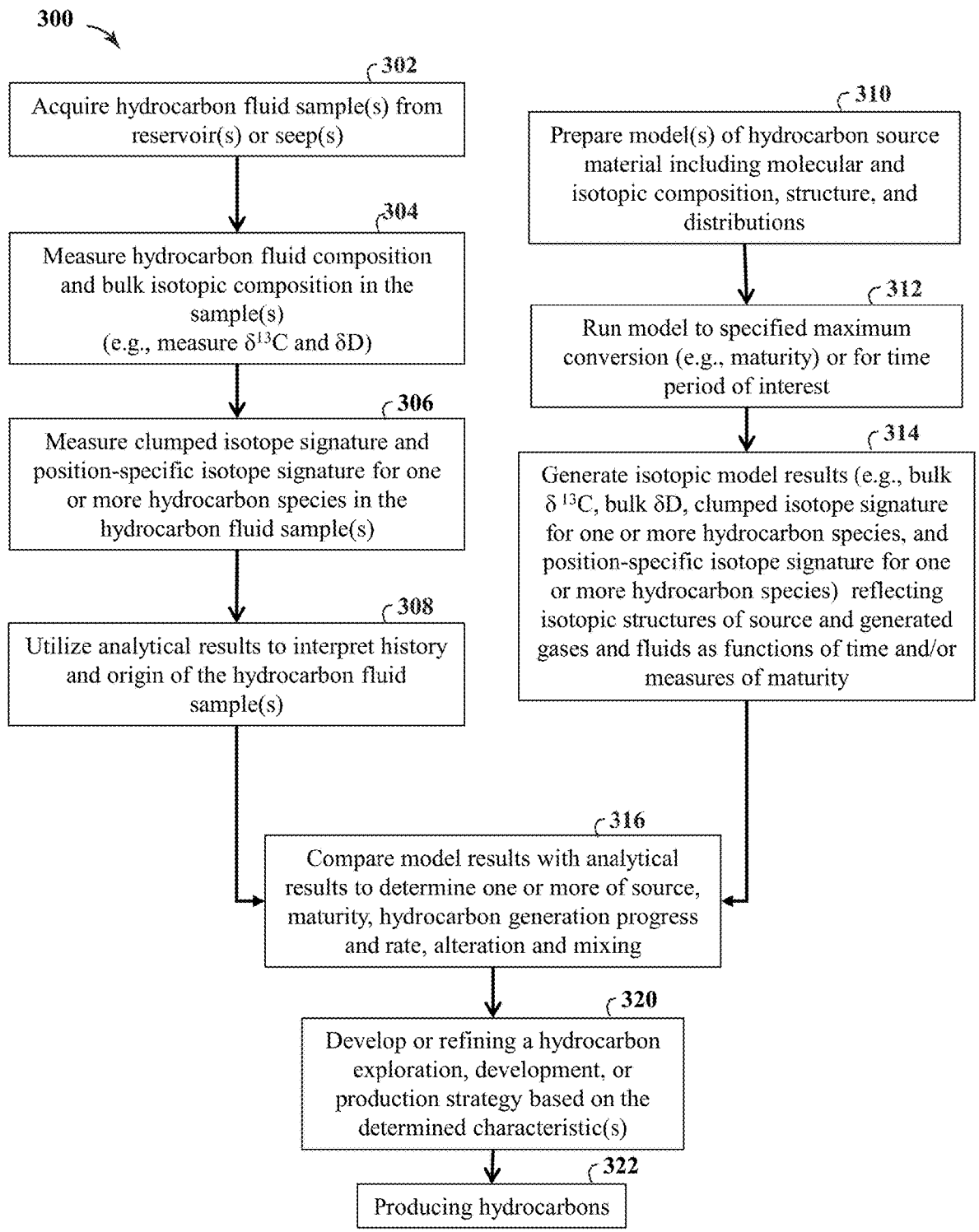
FIG. 3 is a flow diagram of an exemplary methodology in accordance with the present techniques.

FIG. 3 is a flow diagram 300 of an exemplary method in accordance with embodiments of the present techniques. The flow diagram 300 includes the acquisition of a hydrocarbon fluid sample, analysis of the sample to determine a measured/analytical isotopic signature of the sample, preparation of a hydrocarbon source model, generation of isotopic model results, and a comparison of the model results with the analytical results.

At block 302 one or more hydrocarbon fluid samples are obtained. The hydrocarbon fluid samples may be a sample as described above with reference to block 202 of FIG. 2. In some embodiments, the hydrocarbon fluid sample is from a hydrocarbon reservoir or a hydrocarbon seep. In preferred embodiments, the hydrocarbon fluid sample comprises hydrocarbon gases.

At block 304 of FIG. 3, hydrocarbon fluid composition and bulk isotopic compositions of the sample are measured. For example the sample may be analyzed to determine the constituents of the sample, such as types of hydrocarbons (e.g., methane, ethane, propane, etc.), carbon dioxide, hydrogen sulfide, etc. The sample may also be analyzed to determine bulk isotopic composition of the sample, such as the amount of $^{13}C$ in the sample (as a percentage of total carbon content of the sample) and/or the amount of deuterium in the sample (as a percentage of the total hydrogen content of the sample).

At block 306 the sample is analyzed to measure a clumped isotope signature and/or position specific isotope signature for one or more hydrocarbon species in the hydrocarbon fluid sample. The clumped isotope signature and/or position specific isotope signature may be measured as described above with reference to block 204 of FIG. 2.

At block 308 of FIG. 3, the measured clumped isotope signature and/or position specific isotope signature (i.e., analytical results) are used to interpret and provide context on the history and/or origin of the hydrocarbon fluid sample. For example, the bulk isotopic composition and fluid composition data may be used to provide context on the amount of hydrocarbon alteration present in the sample. As another example, the fluid composition data may be used to provide a ratio of the wetness of the sample (i.e. a measure of the ratio of the C2-C4 Content to the C1-C4 content) and thus an indication of the maturity of the sample. This information can then be used to help prepare the model of the hydrocarbon source at block 310 by providing information about what starting materials may be desired in the model.

As an example, the measured data may be integrated with other data/knowledge about the basin. For example, the data may be integrated with analogs from other basins with similar age, maturity, and composition, or with data from other samples taken from the basin that were previously analyzed.

At block 310 a model of the hydrocarbon source material is prepared. This may include identifying the molecular and isotopic composition, structure, and distribution of the starting materials of the model. For example, the starting isotopic composition of the model may comprise identifying the starting bulk $\delta^{13}C$ content, bulk $\delta D$ content, clumped isotope signature for one or more hydrocarbon species, and/or position specific isotope signature for one or more hydrocarbon species. For example, the starting molecular and isotopic compositions may have a stochastic or random distribution or may have a thermodynamically equilibrium distribution. Alternatively, the starting molecular and isotopic compositions may be chosen to have alkyl chains with a certain percentage of alternating $^{13}C$ atoms or a certain percentage of clumped $^{13}C$ atoms. In some embodiments, the starting composition may be indicative of a particular source organism e.g., eukaryotes, archaea, and/or bacteria, or specific subgroups within these domains) which are known to produce lipids that tend to feature alternating sites along a chain with more or less $^{13}C$ and/or lipids that tend to feature clumped $^{13}C$ distribution patterns.

In some embodiments more than one model may be created. For example, multiple models may be created to illustrate a range of starting isotopic signatures for a variety of sources, ranges of maturity of interest, and/or multiple sources in the region of interest.

At block 312 the model is run until the predetermined maximum conversion is reached or for the time period of interest. For example, the model may be run for a specified number of years or millennia. Alternatively, the model may be run until a predetermined conversion is reached, such as a conversion at a particular level of maturity. In some embodiments, the model may be until the free energy of the system is depleted (or reaches a predetermined level), thus indicating that no more cracking will occur.

At block 314 the isotopic model results are generated. This may include generating model results to reflect the isotopic structures of the source and generated gases/fluids as functions of time and/or measures of maturity. For example, the isotopic model results may comprise plots as illustrated in FIG. 5 or 6.

At block 316 of FIG. 3, the model results are compared with the analytical results. The comparison results may be used to determine one or more of source, maturity, hydrocarbon generation progress and rate, alteration, and mixing. The comparison may be as described above with reference to block 208 of FIG. 2.

As another example, the comparison may be used to give an indication of the age of the source facies. For example, isotopic signatures of organic matter are known to change as a function of time. Thus, the model can be used to estimate the signature that results from the source rock at different ages. These different estimated signatures can then be compared with the measured signature to provide an indication of the age of the hydrocarbon reservoir/accumulation from which the sample was obtained.

In some embodiments, the model/simulation may be constrained for different time periods or to provide an indication of fluids that have been lost (e.g., seeped away or dissipated). For example, the model may be constrained to compare the portion of molecules that are created during certain time periods. As another example, the model may be constrained to compare only the portion of molecules that are created at certain levels of conversion. That is, it is known that during the maturation process some of the hydrocarbon fluids seep or dissipate away and are not trapped. Thus, the model may be constrained to look only at those molecules that remain and continue to be trapped, while not looking at the products of those that would have seeped/dissipated away. Therefore, in some embodiments it may be useful to constrain the model to only look at the gas molecules that are produced at certain levels of conversion (for example, from 20-80% conversion, or from 30-60% conversion, or from 40-50% conversion.

At block 320 of FIG. 3 a hydrocarbon exploration, development, or production strategy is developed or refined using the characteristics determined at block 316 and as further described with reference to block 212 of FIG. 2.

At block 322 of FIG. 3 hydrocarbon are produced. The hydrocarbons may be produced as further described above with reference to block 214 of FIG. 2.

Figure 4:
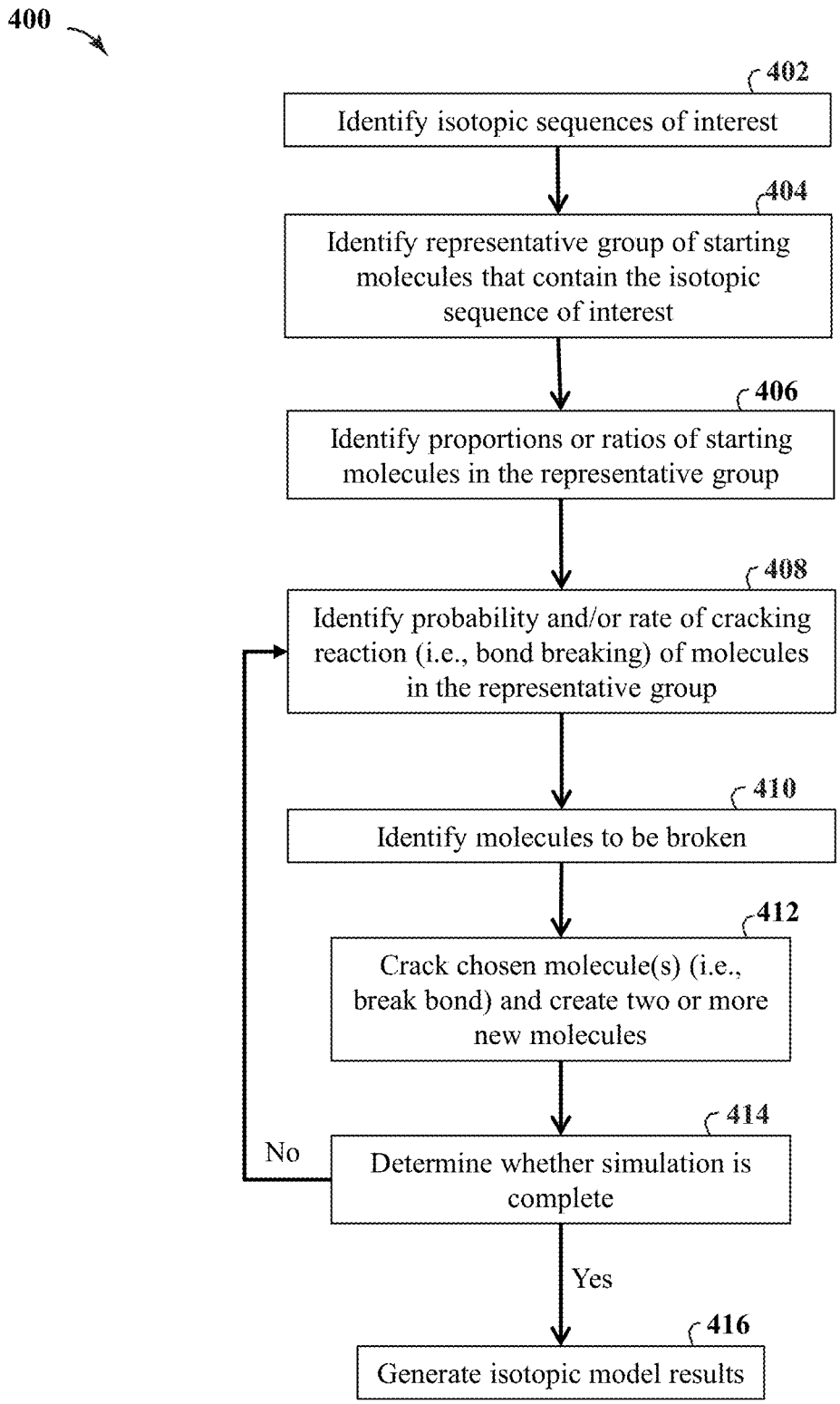
FIG. 4 is a flow diagram of an exemplary methodology for preparing and running simulation models in accordance with the present techniques.

FIG. 4 is an exemplary method of how an isotopic model may be generated. The flow diagram 400 in FIG. 4 may be used in conjunction with block 206 in the flow diagram 200 of FIG. 2 or with blocks 310-314 in the flow diagram 300 of FIG. 3.

At block 402 the isotopic sequences of interest for the model are identified. At block 404 a representative group of staring molecules that contain the isotopic sequence of interest are identified. At block 406 a ratio or proportion of starting molecules in the representative group are identified.

At block 408 the probability and/or rate of the cracking reaction (i.e., bond breaking) of molecules in the representative group is identified. The probability and/or rate may be based on the isotopic structure of the atoms connected by the bond being cracked. For example, the probability and/or rate may be determined so that the bonds are broken to produce the most thermodynamically stable molecules. Alternatively, in some embodiments, the bond that is chosen for cracking may be chosen randomly, such as by a random number generator.

At block 410 the molecules to be broken are identified, and at block 412 the molecule is cracked at the identified bond to form two new molecules.

At block 414 a determination is made as to whether the simulation is completed. For example, the simulation may be run until the system reaches a steady state, until a desired maturity is achieved, or until the desired time step is completed. For example, the simulation may be run until the free energy of the system is depleted or reaches such a level where no more cracking will occur. If the simulation is not complete, the method may return to block 408 where the probabilities/rates of the new system (containing the new cracked molecules) are identified. If the simulation is completed the isotopic model results are generated at block 416.

Figure 7:
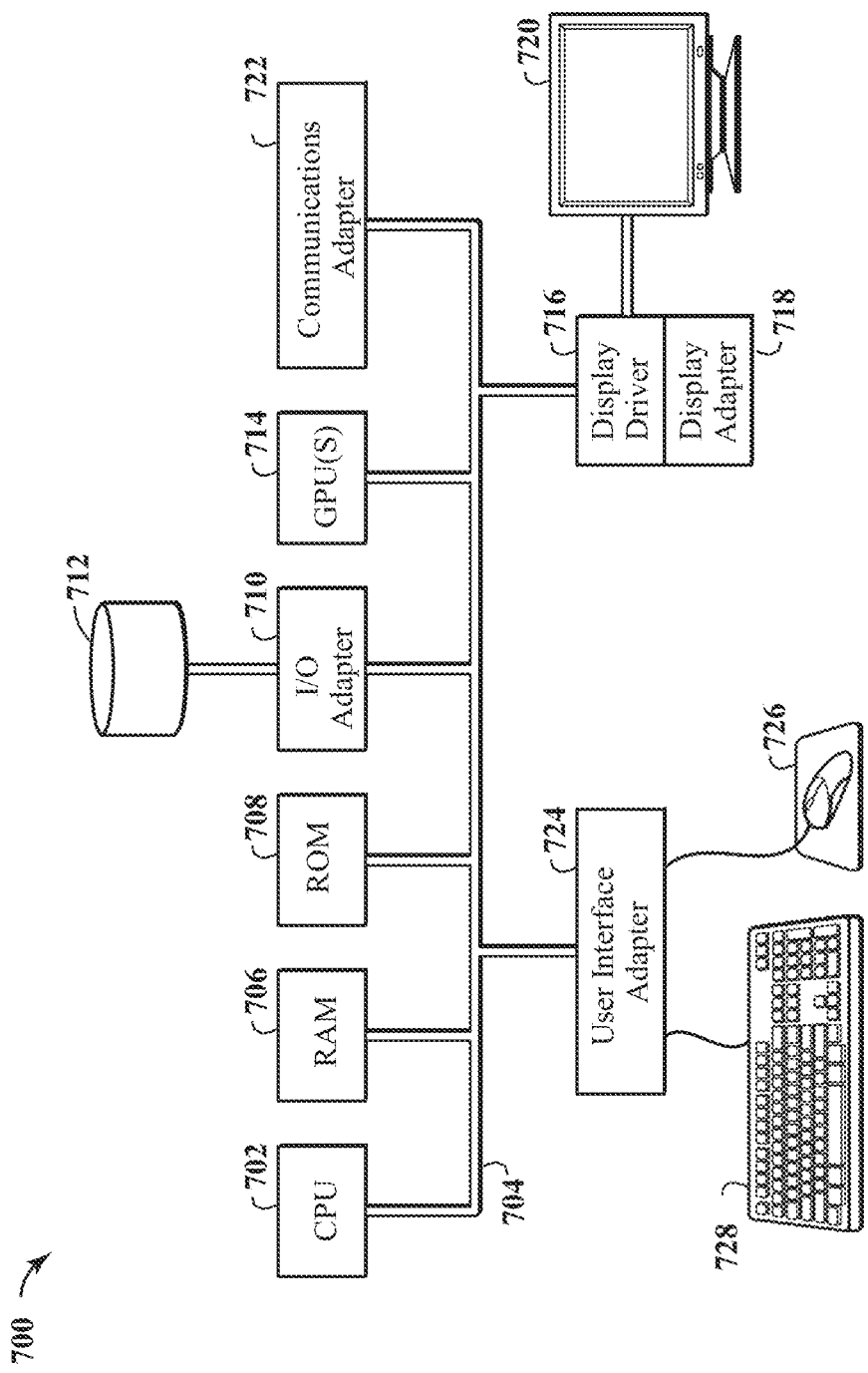
FIG. 7 is a diagram of an exemplary computing system that may be used with the present methodologies and techniques.

FIG. 7 is a block diagram of a computer system 700 which may be used with exemplary embodiments of the present methods. A central processing unit (CPU) 702 is coupled to a system bus 704. The CPU 702 may be any general-purpose CPU, although other types of architectures of CPU 702 (or other components of system 700) may be used as long as CPU 702 (and other components of system 700) support the inventive operations as described herein. The CPU 702 may execute the various logical instructions according to the various exemplary embodiments described herein. For example, the CPU 702 may execute machine-level instructions for processing according to the operation flow diagrams illustrated in FIG. 2, 3 or 4.

The computer system 700 may also include computer components such as a random access memory (RAM) 706, which may be SRAM, DRAM, SDRAM, or the like. The computer system 700 may also include read-only memory (ROM) 708, which may be PROM, EPROM, EEPROM, or the like. RAM 706 and ROM 708 hold user and system data and programs, as is known in the art. The computer system 700 may also include an input/output (I/O) adapter 710, a communications adaptor 722, a user interface adaptor 724, and a display adaptor 718. The I/O adaptor 710, the user interface adaptor 724, and/or communications adaptor 722 may, in certain embodiments, enable a user to interact with computer system 700 in order to input information. The computer system 700 may also include one or more graphic processing units ("GPU(s)") 714 as known in the art.

The I/O adaptor 710 preferably connects a storage device(s) 712, such as one or more of hard drive, compact disc (CD) drive, floppy disk drive, tape drive, etc. to computer system 700. The storage device(s) 712 may be used when RAM 706 is insufficient for the memory requirements associated with storing data for operations of embodiments of the present methods and techniques. The data storage of the computer system 700 may be used for string information and/or other data used or generated as disclosed herein. The communications adaptor 722 may couple the computer system 700 to a network (not shown), which may enable information to be input to and/or output from system 700 via the network (for example, the Internet or other wide-area network, a local-area network, a public or private switched telephony network, a wireless network, and any combination of the foregoing). User interface adaptor 724 Couples user input devices, such as keyboard 728, a pointing device 726, and the like to computer system 700. The display adaptor 718 is driven by the CPU 702 to control, through a display driver 716, the display on a display device 720. Information and/or representations pertaining to a portion of a supply chain design or a shipping simulation, such as displaying data corresponding to a physical or financial property of interest, may thereby be displayed, according to certain exemplary embodiments.

The architecture of system 700 may be varied as desired. For example, any suitable processor-based device may be used, including without limitation personal computers, laptop computers, computer workstations, and multi-processor servers. Moreover, embodiments may be implemented on application specific integrated circuits (ASICs) or very large scale integrated (VLSI) circuits. In fact, persons of ordinary skill in the art may use any number of suitable structures capable of executing logical operations according to embodiments.

As an example, machine-readable logic or code may be used or executed with a computing system, such as computing system 700. The computer system may be used for exploration, production, and development of hydrocarbons. The computer system may include a processor, memory stored in communication with the processor, and a set of instructions stored in memory and accessible by the processor. The set of instructions, when executed by the processor, are configured to: determine a measured geochemical signature of a hydrocarbon sample, where the geochemical signature comprises at least one clumped isotope signature or position specific isotope signature for at least one hydrocarbon species in the sample; determine an expected geochemical signature, wherein the expected geochemical signature comprises at least one clumped isotope signature or position specific isotope signature for at least one hydrocarbon species; compare the measured signature with the expected signature; determining one or more characteristics of the source of the hydrocarbon sample based on the comparison; and/or develop or refine hydrocarbon exploration, development, production strategies.

In some embodiments, the simulations described herein are conducted using a computer system, programmed in accordance with the disclosures herein. Preferably, in order to efficiently perform the simulations, the computer is a high performance computer (HPC), as it is known to those skilled in the art. Such high performance computers typically involve clusters of nodes, each node having multiple CPU's and computer memory that allow parallel computation. The model simulations may be visualized and edited using any interactive visualization programs and associated hardware, such as monitors and projectors. The architecture of the system may vary and may be composed of any number of suitable hardware structures capable of executing logical operations and displaying the output according to the present disclosure. Those of ordinary skill in the art are aware of suitable supercomputers available from Cray or IBM.

EXAMPLES

In order to provide a better understanding of the foregoing discussion, the following non-limiting examples are offered. Although the examples may be directed to specific embodiments, they are not to be viewed as limiting the invention in any specific respect.

In the Examples, bulk isotope abundances are reported in $\delta$-notation and numerical results are reported in per mil (‰), which is obtained by multiplying the $\delta$-notation value by 1000. For example, the bulk $^{13}C$ isotope abundance of a sample may be determined as follows:

$$\delta_{sample} = \frac{(^{13}C/^{12}C)_{sample}}{(^{13}C/^{12}C)_{reference}} - 1$$

where the reference is the Vienna PeeDee Belemnite ("V-PDB") standard.

In the Examples, clumped isotope abundances are reported in $\Delta$-notation and numerical results are reported in per mil (‰), which is obtained by multiplying the $\Delta$-notation value by 1000. For example, the clumped isotope abundance of $^{13}C/^{13}C$ may be determined as follows:

$$\Delta_{sample} = \frac{(^{13}C^{13}C/^{12}C^{12}C)_{sample}}{(^{13}C^{13}C/^{12}C^{12}C)_{reference}} - 1$$

where the reference is the stochastic distribution of a material with the same bulk $\delta^{13}C$ as the sample.

Example 1

Ethane Cracking

The kinetic Monte Carlo methods described herein were used to simulate the cracking of ethane with an initial stochastic distribution of $^{13}C$ substitutions. In the simulations, the imposed kinetic isotope effects were very small ($k_{1213}/k_{1212}=0.997$ and $k_{1313}/k_{1212}=0.992$) in order to confirm that the influence of small kinetic isotope effects could be detected in the amount of $^{13}C^{13}C$ isotopologues present.

Figure 8:
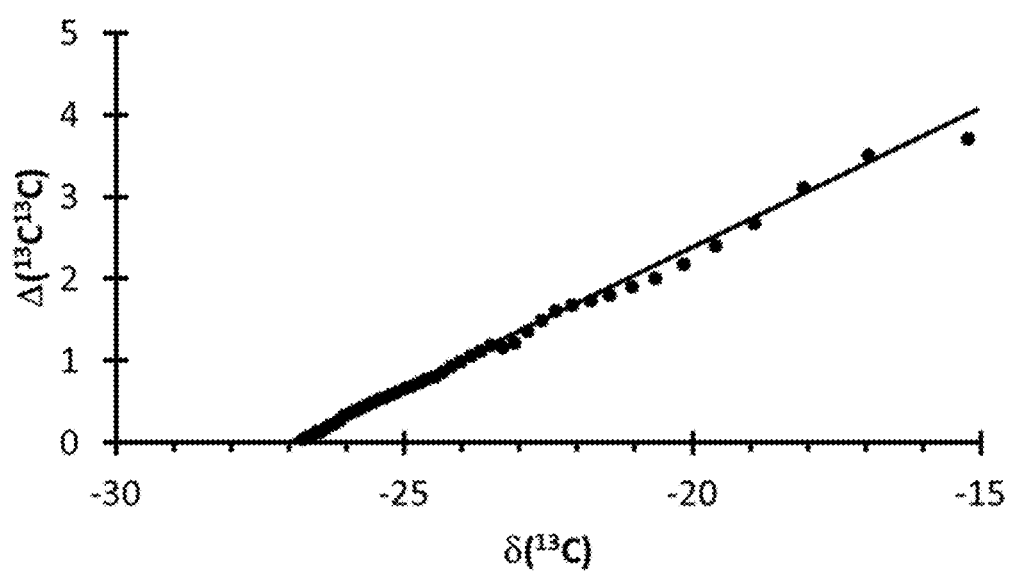
FIG. 8 is a plot comparing an analytical solution to a kinetic Monte Carlo simulation of the amount of $^{13}$C$^{13}$C isotopologues as a function of bulk $^{13}$C content of the residual ethane after irreversible first-order cracking.

The results from over 480,000 simulations each starting with $2 \times 10^6$ ethane molecules with an average bulk composition of $\delta^{13}C=-27.0\%0$ (as compared to the V-PDB standard) are compared with the analytical solution in FIG. 8 (which plots the amount of doubly-$^{13}C$-substituted ethane isotopologues as a function of the bulk $^{13}C$ content of the residual ethane after irreversible first order cracking). The solid line in FIG. 8 is from the analytical solution and the dotted points are from the averaged kinetic Monte Carlo simulations.

It is desirable for the kMC simulations described herein to provide results that are equivalent to those from a continuum differential equations approach. FIG. 8 shows the amount of the clumped $^{13}C^{13}C$ ethane isotopologue as a function of the bulk $^{13}C$ content for the residual ethane after cracking stochastically distributed ($\delta^{13}C=-27.0\%_o$) ethane. In the first-order cracking model, the expected behavior is for the amount of each isotopologue to decrease as e with the appropriate rate constant, k.

As seen in FIG. 8, the $\Delta(^{13}C^{13}C)$ starts at zero, as appropriate for a stochastic distribution, and then rises along with $\delta^{13}C$ as the cracking proceeds. Thus, both series increase as a function of time and $\Delta(^{13}C^{13}C)$ increases as $\delta^{13}C$ increases. The latter increases because the $^{12}C^{13}C$ bonds break more slowly than do the predominant $^{12}C^{12}C$ bonds, and the former increases because the $^{13}C^{13}C$ bonds break more slowly leading to the number of $^{13}C^{13}C$ molecules being larger than the stochastic amount for a given bulk $\delta^{13}C$. As seen in FIG. 8, the kMC results generally follow the analytical solution for early times (with $\delta^{13}C$ near the starting level), but at very late stages of the simulation with high $\delta^{13}C$ and high $\Delta(^{13}C^{13}C)$, the kMC results are seen to scatter around the analytical results. This is likely due to the very small number of molecules remaining in the simulation.

The results shown in FIG. 8 confirm that the simulation can match analytical solutions and that interesting rare species can be generated and their properties followed as a function of the extent of destruction of the parent molecules.

Example 2

Cracking Large Alkanes

Figure 9A:
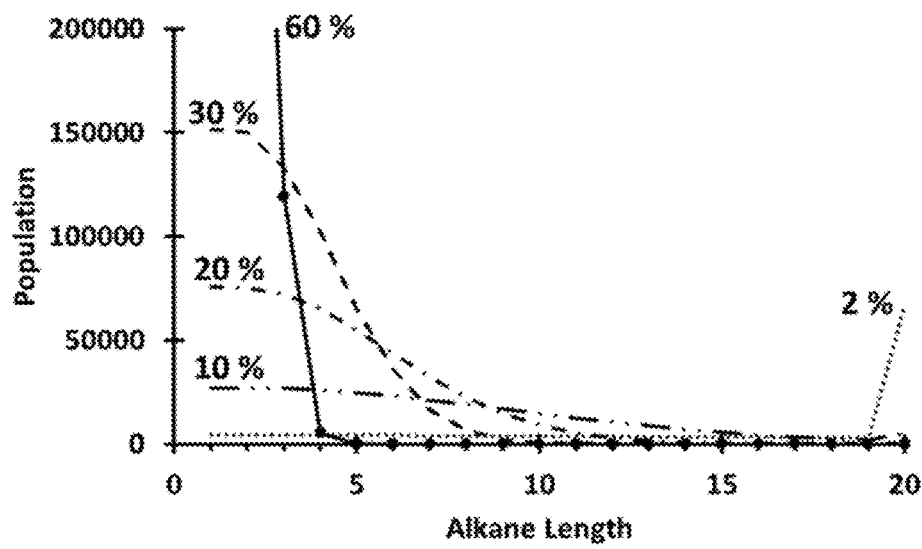
FIGS. 9A and 9B plot molecular distributions resulting from the cracking of nC$_{20}$ alkanes according to kinetic Monte Carlo simulations of a first-order irreversible cracking model.
Figure 9B:
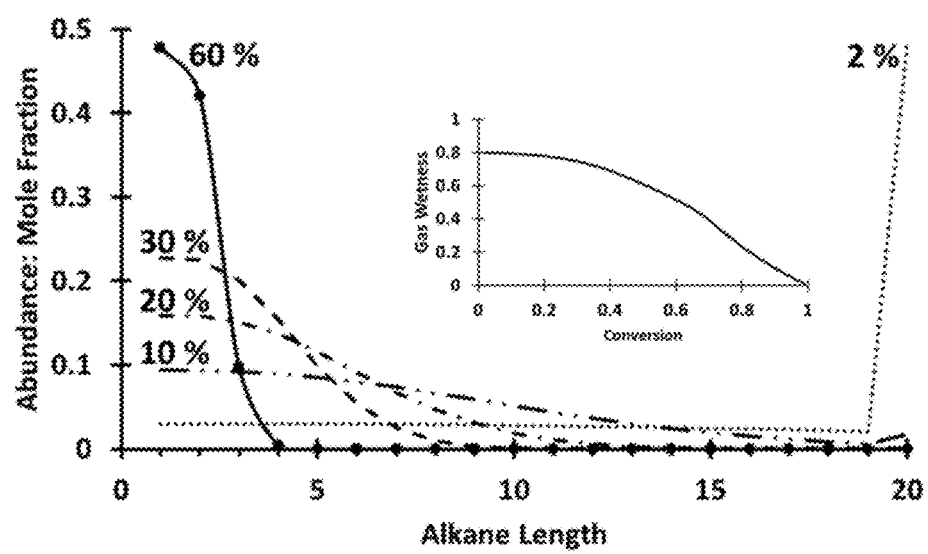

The kinetic Monte Carlo methods described herein were used to simulate the first-order irreversible cracking of $10^5$ $nC_{20}$ molecules with an initial stochastic distribution of $^{13}C$ atoms. FIG. 9A shows the number of molecules present in the simulation compared to the alkane length (carbon number), and FIG. 9B shows the mole fraction of each species of hydrocarbon as compared to the alkane length. In both FIGS. 9A and 9B, the conversion (i.e., fraction of initial bonds broken) is shown near each curve. The inset chart in FIG. 9B shows the Gas Wetness (defined here as $C_1$/sum ($C_1$-$C_5$)) as a function of the conversion.

As described above, FIGS. 9A and 9B show the molecular proportions (ignoring isotopic content) of the different sizes of alkanes for various levels of conversion (i.e., the fraction of the initial bonds in the system). As illustrated in the figures, the observed populations shifted with increasing conversion, from the initial population to a broad distribution including all sizes of alkanes, to mostly small gas molecules at high conversion).

Additionally, as seen in FIGS. 9A and 9B, after 2% conversion, the number of initial $nC_{20}$ molecules fell by a noticeable amount and the number of smaller product molecules was essentially independent of their size. Near the start of the simulation, only $nC_{20}$ molecules are present so almost the only events able to be selected are the breaking of bonds within these molecules. This explains the rapid drop for molecules where n=20. Ignoring, the small KIE, each of the bonds in the $nC_{20}$ molecules has the same chance of being selected, and this determines the even distribution of smaller product molecules. For example, $nC_{20} \rightarrow nC_1 + nC_{19}$ and $nC_{20} \rightarrow nC_2 + nC_{18}$ ... can occur via the breakage of two bonds in each molecule and $nC_{20} \rightarrow 2nC_{10}$ to can occur with the breakage of one bond, but producing 2 of the same type of product molecule. Hence, the number of each size of the product molecule produced from a population of initial $nC_{20}$ molecules is about the same. If position-dependent rates were incorporated into the kMC rules, this even distribution would be modified.

As conversion proceeds, the distributions shift towards smaller molecules. After 30% of the bonds have been broken, there are almost no remaining source molecules and after 60% conversion, the largest molecules present in any significant amount are smaller than pentane. This corresponds qualitatively with the shift from solid sources to oil to gas in real petroleum systems as they undergo catabolic transformations. The kMC simulations, thus, captured the expected shift in molecule size and, if the simulations were run to exhaustion, the production of pure methane. Thus, in the simple alkane-only model, all of the source is converted to small molecules, while, in reality one would expect low-H-content large molecules to be present along with the small alkanes at high conversion.

Figure 10:
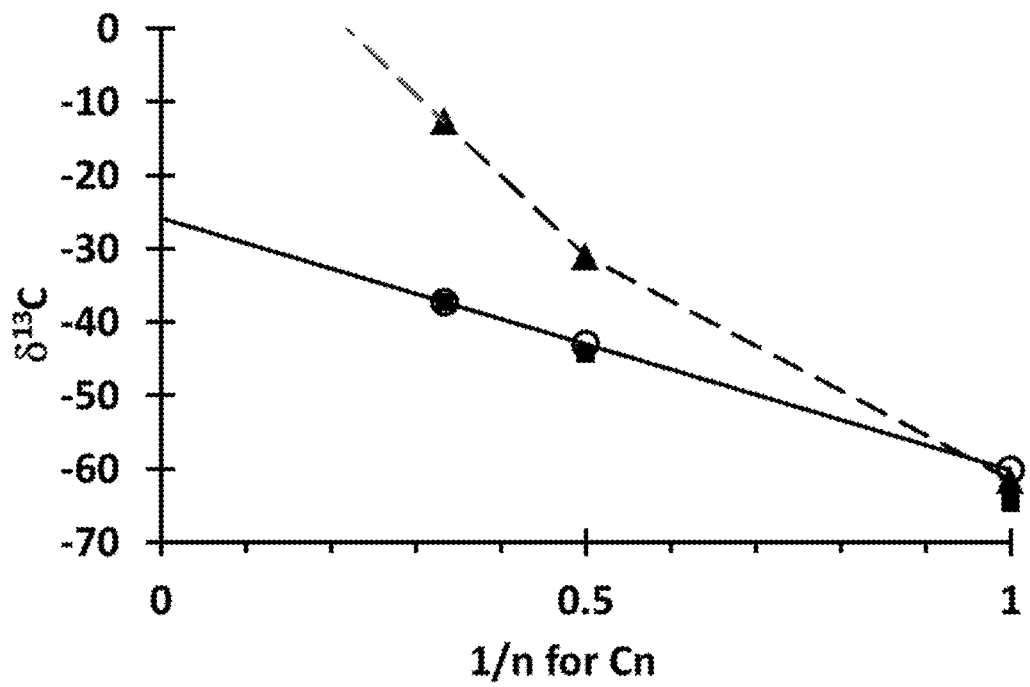
FIG. 10 is a plot of the bulk $^{13}$C isotope content for small alkanes of length n from a kinetic Monte Carlo simulation of nC$_{20}$ cracking via a first-order irreversible cracking model.

FIG. 10 provides an illustration of the bulk $^{13}C$ isotopic content of molecules of different sizes. In particular, FIG. 10 is a plot of the $\delta^{13}C$ content versus $1/n$ for small alkanes of length n that resulted from the kinetic Monte Carlo simulation of $nC_{20}$ cracking via a first-order irreversible model. In FIG. 10, the open circles represent data at 4% conversion, the filled squares at 10% conversion, and the filled triangles at 50% conversion. The solid line in FIG. 10 is a best fit line for the 4% conversion data and the dashed line joins the points of the 50% conversion data.

The plot shown in FIG. 10 can be explained by considering the KIE is larger on the bulk isotopic content of smaller molecules. The (primary) KIE influences only the atom of the gas molecule that was bonded to the residue, but not the other atoms. Thus, the larger gas molecules (which have a greater number of atoms) simply inherit the average isotopic content of the source. These effects lead to the $1/n$ form of FIG. 10, as $1/n$ carbon atoms of each molecule are affected by the KIE.

Extrapolating the points to an infinitely sized molecule yields $\delta^{13}C$ very near the initial content of the starting molecules, as expected. At higher conversions, the data from the kMC no longer falls on a straight line and extrapolate to much higher $\delta^{13}C$, exemplifying the nontrivial effects that can be produced by a robust model that faithfully simulates the entire catabolic conversion scheme including secondary cracking. The enhanced $\delta^{13}C$ for ethane and propane at high conversions is due, at least in part, to the delayed cracking of those molecules that contain one (or possibly two) $^{13}C$ atoms, a further influence of the KIE. Interpretations of deviations from linearity based on the natural gas often involve the presence of alternative sources of methane, but as seen in the figures, we can also see that they can result from extended secondary cracking of ethane and propane, etc. The magnitudes of $\delta^{13}C$ for methane-propane shown here are larger in some regions than what is commonly observed for thermogenic gases in nature. This may be due to (1) the very high extent of reaction developed in the later stages of the kMC simulation and (2) because of the magnitude of the KIE imposed (i.e., 3% KIE) in the simulation which may be larger than what typically occurs in petroleum systems.

Figure 11:
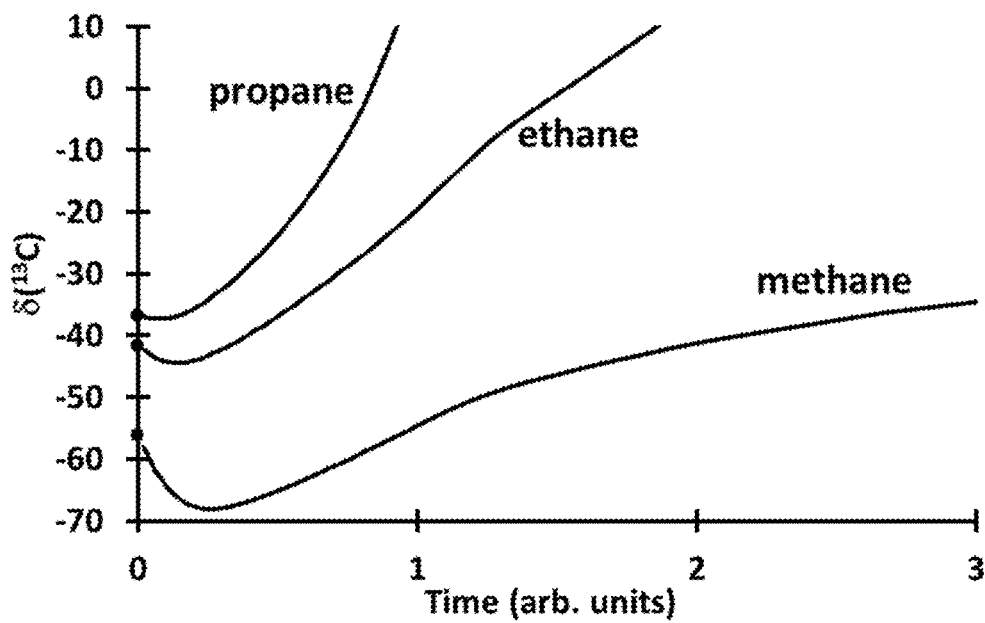
FIG. 11 is a plot of $^{13}$C content of methane, ethane, and propane over time from the cracking of a nC$_{20}$ alkanes with an initially random distribution of $^{13}$C.

FIG. 11 provides an illustration of the bulk isotopic content of the small gases generated in the cracking simulation. For each of the gases illustrated in FIG. 11, the $^{13}C$ content decreases for a period of time before increasing. The magnitude of the decease is largest for methane and the slope of the curve after the decrease is largest for propane.

In FIG. 11 as in the natural gas plot of FIG. 10, the abundances of $^{13}C$ decreases with increasing carbon number. Typical descriptions of natural gases, have $\delta^{13}C$ becoming progressively enriched as maturity increases, while the curves in FIG. 11 show first a depletion, and then an enrichment. The trends observed in the simulation results are consistent, however, with cumulative gas capture from laboratory pyrolysis of shales.

terminal depletion, and the curves seen in FIG. 11 start to increase with time or conversion. Thus, while different portions of the source molecules in real systems might have both different $^{13}C$ content and different cracking rates and, thereby, lead to non-monotonic behavior in the content of generated gases, no such effect is necessary to model in the kMC simulation to get the behavior shown in FIG. 11.

Table 1 provides more detailed results from the cracking simulations that started with $nC_{20}$ alkanes, an initial $\delta^{13}C=-27‰$, and a 3% kinetic isotope effect. Table 1 also provides gross measures of maturity (gas wetness and dryness) and the mole fractions of selected alkanes from methane to the source $nC_{20}$ molecules, all as a function of conversion. This level of detail is available from the kMC simulation and highlights the ability of this approach to provide an integrated view of hydrocarbon molecular and isotopic chemistry.

TABLE 1

| Conv.* | Wetness# | Dryness+ | $\delta C_1$ | $\delta C_2$ | $\Delta_{1313}$ | $\delta C_3$ | $\Delta_{121213}$ | $\Delta_{121312}$ | $\Delta_{131213}$ | $\Delta_{121313}$ | $\Delta_{131313}$ |
|---|---|---|---|---|---|---|---|---|---|---|---|
| 0.02 | 0.799 | 1.251 | −58.241 | −42.358 | −0.324 | −37.013 | −5.506 | 11.020 | −10.950 | 5.401 | −12.572 |
| 0.10 | 0.794 | 1.259 | −64.655 | −44.330 | 0.204 | −37.253 | −7.183 | 14.383 | −14.506 | 6.875 | −1.348 |
| 0.20 | 0.780 | 1.283 | −67.872 | −43.816 | −0.282 | −35.105 | −8.613 | 17.237 | −17.112 | 8.294 | −1.123 |
| 0.30 | 0.749 | 1.336 | −67.407 | −41.018 | −0.302 | −30.601 | −9.622 | 19.259 | −19.161 | 9.237 | −0.576 |
| 0.40 | 0.693 | 1.443 | −65.082 | −36.749 | −0.397 | −23.641 | −10.712 | 21.448 | −21.387 | 10.179 | −0.350 |
| 0.50 | 0.614 | 1.628 | −61.513 | −31.100 | −0.401 | −12.676 | −12.429 | 24.886 | −24.565 | 11.655 | −0.717 |
| 0.59 | 0.522 | 1.916 | −56.766 | −23.444 | −0.383 | 7.032 | −16.176 | 32.401 | −31.969 | 14.923 | −1.877 |
| 0.71 | 0.373 | 2.682 | −49.555 | −9.039 | −0.414 | 85.889 | −34.612 | 69.412 | −67.963 | 30.416 | −23.707 |
| 0.81 | 0.218 | 4.593 | −44.439 | 4.235 | −0.729 | | | | | | |
| 0.91 | 0.093 | 10.801 | −38.057 | 26.986 | −1.457 | | | | | | |
| 0.99 | 0.010 | 104.263 | −29.434 | 96.731 | −3.588 | | | | | | |

| Conv. | $C_1$ | $C_2$ | $C_3$ | $C_4$ | $C_6$ | $C_8$ | $C_{10}$ | $C_{12}$ | $C_{14}$ | $C_{16}$ | $C_{20}$ |
|---|---|---|---|---|---|---|---|---|---|---|---|
| 0.02 | 0.0304 | 0.0304 | 0.0304 | 0.0302 | 0.0298 | 0.0290 | 0.0280 | 0.0268 | 0.0254 | 0.0238 | 0.4833 |
| 0.10 | 0.0938 | 0.0937 | 0.0925 | 0.0899 | 0.0801 | 0.0663 | 0.0511 | 0.0366 | 0.0245 | 0.0152 | 0.0178 |
| 0.20 | 0.1588 | 0.1583 | 0.1513 | 0.1368 | 0.0912 | 0.0473 | 0.0192 | 0.0061 | 0.0015 | 0.0003 | |
| 0.30 | 0.2279 | 0.2258 | 0.2004 | 0.1538 | 0.0538 | 0.0100 | 0.0010 | 0.0001 | | | |
| 0.40 | 0.3029 | 0.2963 | 0.2238 | 0.1208 | 0.0108 | 0.0002 | | | | | |
| 0.50 | 0.3857 | 0.3662 | 0.1938 | 0.0489 | 0.0002 | | | | | | |
| 0.59 | 0.4780 | 0.4206 | 0.0971 | 0.0043 | | | | | | | |
| 0.71 | 0.6271 | 0.3706 | 0.0023 | | | | | | | | |
| 0.81 | 0.7823 | 0.2177 | | | | | | | | | |
| 0.91 | 0.9074 | 0.0926 | | | | | | | | | |
| 0.99 | 0.9904 | 0.0096 | | | | | | | | | |

*Conv. = convergence defined as fraction of initial bonds broken
Wetness = sum($C_2 - C_5$)/sum($C_1 - C_5$)
+Dryness = 1/Wetness Initially generated gases are depleted in $^{13}C$, and the KIE acts to decrease the rate of bond-breaking for bonds between C atoms with at least one $^{13}C$ substitution. However, it is not only the gas molecules that have their newly formed terminal atoms depleted in $^{13}C$, as the same holds for the residual portion of the parent molecule. Thus, after some cracking has occurred, part of the population of molecules eligible for generating new gas molecules is also lighter at the ends than is the original population. As such, cracking from these modified source molecules will yield gas molecules lighter in overall $^{13}C$ content than the initially produced gas molecules because both of their ends (for molecules larger than methane) will be influenced by the KIE, while it influences only one end of the initial population of gas molecules.

While the newly formed termini of all of the molecules that result from cracking are depleted in $^{13}C$, the overall bulk content of the residual molecules is increasing in $^{13}C$ content. Since the total is unchanged, the gases are lighter overall. This effect eventually wins out over the effect of the Example 3

Doubly-Clumped Ethane from Alkane Cracking

In the following example kinetic Monte Carlo simulations were conducted for three different starting configurations of $nC_{20}$ molecules. The different simulations had the same bulk $^{13}C$ content, but the $^{13}C$ isotopes were distributed differently. In the "random" case, the $^{13}C$ atoms were simply distributed randomly among the $^{13}C$ atoms. In the "avoid" case, the $^{13}C$ atoms were given a propensity to avoid being on adjacent sites in the molecules. In the "clumped" case, the $^{13}C$ atoms were given the propensity to prefer occupying adjacent sites in the molecules. The distributions were created with preliminary Metropolis Monte Carlo simulations.

Figure 12:
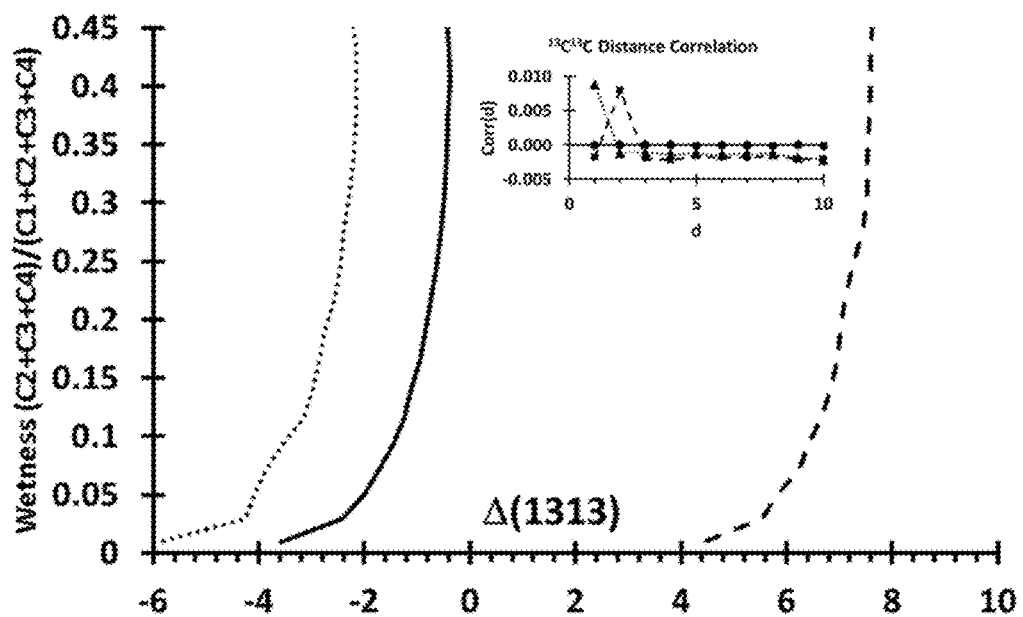
FIG. 12 is a plot of gas wetness versus clumped isotope signature in ethane from kinetic Monte Carlo simulations.

FIG. 12 illustrates a comparison of the gat wetness and clumped isotope signatures of the resulting molecules from the kinetic Monte Carlo simulation. Each of the simulations started with $nC_{20}$ molecules and a system bulk $\delta^{13}C$ of −27‰. As described above, each system started with a different distribution of $^{13}C$ atoms and in FIG. 12 the dotted line represents the "avoid" case, the solid line represents the "random" case, and dashed line represents the "clumped" case. The inset in FIG. 12 shows a plot of the distance-distance correlation functions for the three cases.

From the results shown in FIG. 12 it is seen that the initial value of the clumped isotope signature in ethane resulting from the cracking is sensitive to the distribution of $^{13}C$ in the starting material. The simulation in the "random" case with random $^{13}C$ positioning gave $\Delta(^{13}C^{13}C)$ of about 0, while the simulation in the "avoid" case that had a preference for avoiding $^{13}C$ atoms at adjacent sites tended to have a negative initial $\Delta(^{13}C^{13}C)$, and the simulation in the "clumped" case that had a preference for clumping the $^{13}C$ atoms at adjacent sites tended to have a positive $\Delta(^{13}C^{13}C)$. In each case, for the different simulations the shape of the curves in FIG. 12 are similar to one another. At high wetness (i.e., low maturity), the $\Delta(^{13}C^{13}C)$ remained almost constant as the maturity increased and wetness fell, and then it decreased more strongly with maturity at higher maturity/lower wetness.

The results shown in FIG. 12 make sense, in that a system with $^{13}C$ atoms clumped together would exhibit higher levels of the doubly-substituted ethane as there are more fragments present in the starting material that can become doubly-substituted species upon cracking. Similarly, if the $^{13}C$ atoms avoid one another, the number of such fragments is less than in the random system. Thus, the kMC results seem to be consistent with the interpretation that the general trends and magnitude of the clumped isotope signatures in a suite of gases of various maturities are generated by kinetic isotope effects in the chemical reactions that both form and destroy the ethane.

Example 4

Propane Position-Specific $^{13}C$ and Source Size Effects

Figure 13:
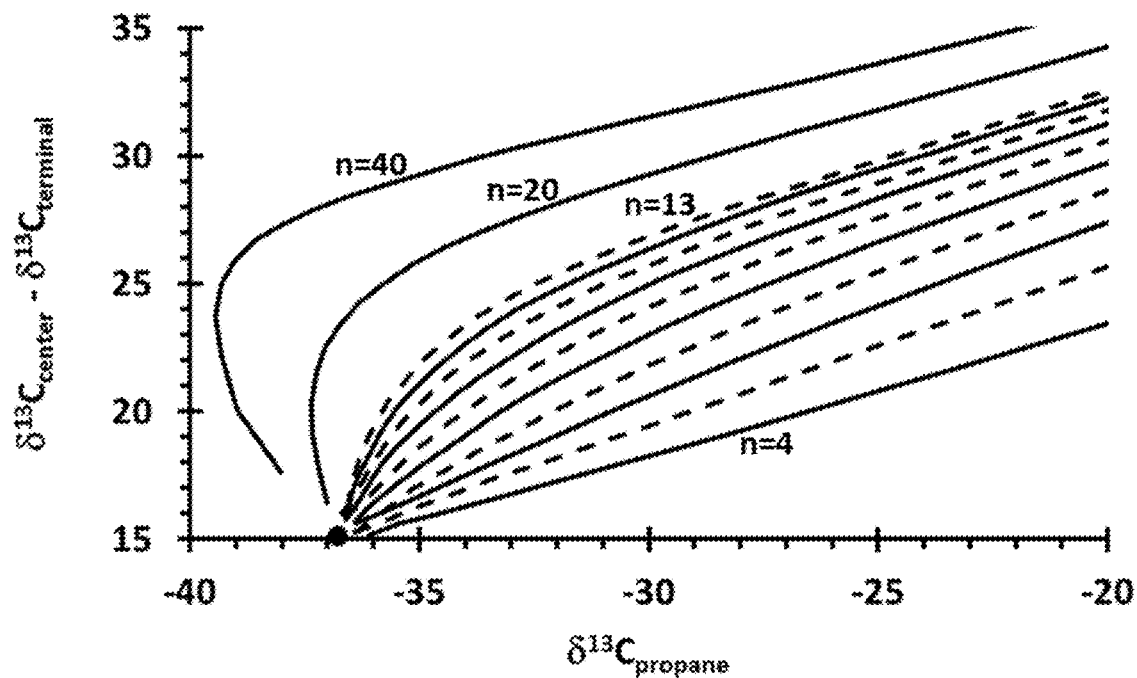
FIG. 13 is a plot of position-specific isotopologues of propane generated from cracking linear alkanes.

In this example, kinetic Monte Carlo simulations ($k_{1213}/k_{1212}$=0.97 and $k_{1313}/k_{1212}$=0.9409) were performed for various lengths of alkanes all of which had the same $\delta^{13}C$ content (−27‰). FIG. 13 shows a plot of the position-specific effect (terminal vs. central) of the $^{13}C$ on the generated propane molecules.

In this example, alkanes with a bulk $\delta^{13}C$ content of −27‰ and a random distribution of $^{13}C$ were cracked, and the $^{13}C$ content of the central and terminal carbon atoms were followed as a function of conversion. From the lowest to the highest curves shown in FIG. 13, the starting alkanes were $nC_4$, $nC_5$, $nC_6$, $nC_7$, $nC_8$, $nC_9$, $nC_{10}$, $nC_{11}$, $nC_{12}$, $nC_{13}$, $nC_{20}$, and $nC_{40}$, respectively. The large filled circle in FIG. 13 represents the initial propane generated, which is independent of the starting molecular size according to a stochastic model (position −36.75, 15.15 on FIG. 13). In FIG. 13, even-numbered alkanes are shown with solid lines and odd-numbered alkanes are shown with dotted lines.

As can be seen in FIG. 13, the propane center position is always enriched relative to the terminal position in this model. The generated propane is relatively light relative to the starting material (which is consistent with the simulations seen in FIG. 10) and all of the curves appear to start from the same point at $\delta^{13}C$ of approximately 36.7 and $\delta^{13}C_{center}$-$\delta^{13}C_{terminal}$ of approximately 15. For shorter alkanes, the center vs. terminal difference increases as the bulk isotopic content of the propane increases, but for large-enough starting alkanes (such as the $nC_{20}$ and $nC_{40}$ alkanes in FIG. 13), the bulk isotopic content first decreases, then increases with the center vs. terminal difference always increases.

The curves in FIG. 13 can be explained as follows. Considering a stochastic distribution of $^{13}C$ atoms in any n-alkane with a length≥4, the probability of occurrence of each possible pattern of $^{13}C$ atoms in the terminal 4 atoms of the chain is $p^m(1-p)^{4-m}$ where p is the fraction of any given site being occupied by $^{13}C$ (p=0.1076) for $\delta^{13}C$=−27‰ vs. PDB) and m is the number of $^{13}C$ atoms in the fragment. The initial amount of propane generated in a small unit of time, δt, from each of these 4-atom fragments is proportional to kδt where k is the bond-breaking rate constant for the bond of interest (the one connecting the $4^{th}$ and $3^{rd}$ atoms from the end of the molecule). Each such fragment produces propane which inherits the $^{13}C$ content and distribution from the terminal three atoms of the fragment. Using the relative rates, including KIEs, appropriate to the data in FIG. 13, calculating $p^m(1-p)^{4-m}$, and summing up equivalent species, we find that the initial $\delta^{13}C$=−36.73 and $\delta^{13}C_{center}$-$\delta^{13}C_{terminal}$=−15.15. This point is shown as the filled circle in FIG. 13. Thus, the kMC simulation starting from a stochastic distribution, independent of the length of the alkane, gives the expected isotopic content and distribution for the initially generated propane.

The initial propane is lighter than the source material, due to the KIE associated with breaking the bond that leads to liberating the propane. The kMC simulation of the first-order model continues to simultaneously generate propane (and other small molecules) from both previously un-cracked source molecules and from secondary cracking of product molecules (which might be considered as residue of the source or as oil cracking to gas). For relatively small source molecules, both $\delta^{13}C$ and $\delta^{13}C_{center}$-$\delta^{13}C_{terminal}$ increase monotonically as conversion increases. The former increases because of two effects. First, the residual source molecules from which "new" propanes are generated become $^{13}C$-enriched as conversion proceeds because lighter molecules are more likely to have reacted earlier. Second, some propane cracks, even at early stages of conversion, and for the same reasons as for the source molecules, the residual propane is $^{13}C$-enriched compared to the propane molecules that have cracked. The initial $\delta^{13}C_{center}$-$\delta^{13}C_{terminal}$ is positive, indicating the center position is enriched relative to the terminal, because when the bond between the $3^{rd}$ and $4^{th}$ atoms from the end of the source molecule is cleaved, the fragment is more likely than average to have $^{12}C$ at the newly formed terminal position.

As described above, it is not only the product propane molecules that have light ends. The atoms at the end of the residuum are also likely to be depleted in $^{13}C$ due to the KIE. This means that the next propane generated from the residuum is likely to be depleted in both terminal methyl groups and to have $\delta^{13}C$ even lower than the initially generated propane. This lead to $\delta^{13}C_3$ decreasing as the center vs. terminal signature increases even faster than occurs with the smaller molecules. These effects are apparent in the curves in FIG. 13.

Figure 14:
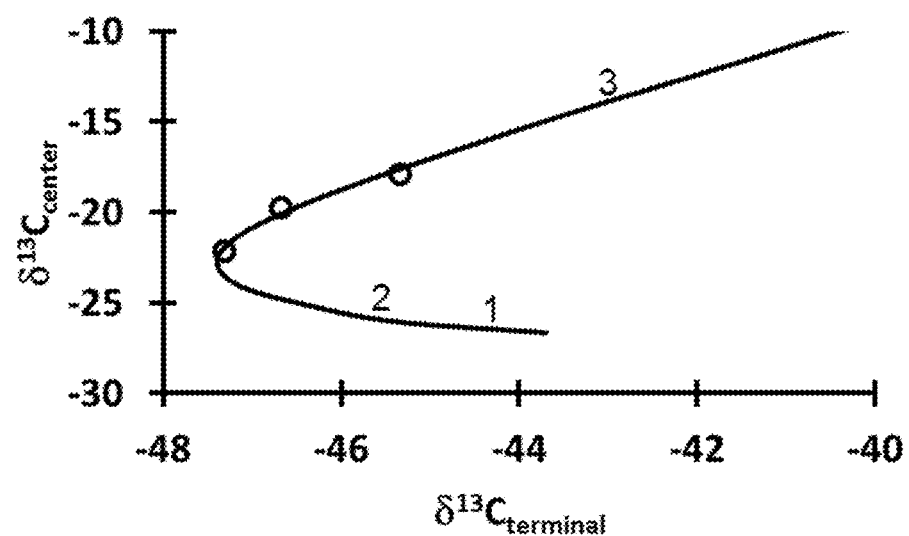
FIG. 14 is a plot of center $^{13}$C propane molecules versus terminal $^{13}$C propane molecules from kinetic Monte Carlo simulations.

FIG. 14 was generated from simulations starting from $nC_{40}$ with a random distribution of $^{13}C$ atoms and an initial $\delta^{13}C$=−27‰(corresponding to the top curve in FIG. 13). The start of the curve in FIG. 14 at low maturity (2% conversion) is at the bottom center with $\delta^{13}C_{terminal}$=−43.70, $\delta^{13}C_{center}$=−26.66. The reference for δ in this figure is V-PDB. The open circles in FIG. 14 are from the hydrous pyrolysis experiments reported in Piasecki et al. (2018) "Position-Specific $^{13}$C Distributions from Propane with Experiments and Natural Gas Samples", *Geochimica et Cosmochimica Acta*, Vol. 220, pp. 110-124 (referred to herein as "Piasecki 2018"), and have been converted to cumulative samples and shifted to fit on the curve to account for the different references and different source material.

In FIG. 14, the $\delta^{13}C_{center}$ for the central position in propane is plotted directly against the $\delta^{13}C_{terminal}$. The curve starts at the lower right and moves to the left (lower $\delta^{13}C_{terminal}$) and slightly higher in $\delta^{13}C_{center}$. After reaching a minimum in $\delta^{13}C_{terminal}$, both measures increase as maturity progresses to higher conversion. This figure can be compared to FIGS. 3 and 4 in Piasecki 2018 but the reference substances are different (and hence the absolute magnitudes cannot be compared directly). In this example, the V-PDB standard was sued while in Piasecki 2018 a particular laboratory reference gas was used and the center and terminal references are the corresponding values for those positions in that reference gas. The open circles are from the hydrous pyrolysis experiments of Piasecki 2018. These have been shifted before being placed on the plot for two reasons. First, the actual samples were collected sequentially; the lowest $\delta^{13}C_{terminal}$ sample represents gases from 330° C. pyrolysis which were removed from the system before further 360° C. pyrolysis was performed; and those gases were removed before a final 390° C. pyrolysis was performed. Further, the data in Piasecki 2018 was converted to cumulative samples, to be compared to be compared with the cumulative curve in FIG. 14, by assuming that each sample was of the same number of moles of propane and reconstructing the $^{13}$C content of the entire gas production up through the sampling time for each point. The second shift was to move the points, all by the same amount, to reflect the different references used (unknown in the case of the experiments) and the different starting materials. The correspondence is merely intended to be illustrative.

All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted.

The invention claimed is:

1. A method for determining one or more characteristics of a hydrocarbon source, comprising:
    obtaining a hydrocarbon fluid sample;
    analyzing the hydrocarbon fluid sample to determine at least one measured clumped isotope signature or measured position specific isotope signature for at least one hydrocarbon species in the hydrocarbon fluid sample;
    determining at least one expected clumped isotope signature or expected position specific isotope signature, where the expected clumped isotope signature or expected position specific isotope signature are determined from a model that reflects different source compositions, isotopic structures, and kinetic processes, and wherein the model is solved using a kinetic Monte Carlo simulation;
    comparing the measured clumped isotope signature or measured position specific isotope signature with the expected clumped isotope signature or expected position specific isotope signature;
    determining at least one characteristic of the source of the hydrocarbon sample based on the comparison; and
    developing or refining a hydrocarbon exploration, development, or production strategy based at least in part on the determined characteristic.

2. The method of claim 1, wherein the hydrocarbon fluid sample comprises hydrocarbons and associated gases.

3. The method of claim 2, wherein the associated gases comprise carbon dioxide.

4. The method of claim 1, wherein the hydrocarbon fluid sample comprises at least one of methane, ethane, propane, butane, pentane, hexane, heptane, octane, nonane, decane, and combinations thereof.

5. The method of claim 1, wherein the hydrocarbon fluid sample is a gas sample.

6. The method of claim 1, wherein the position specific isotope signature of a hydrocarbon species identifies the difference between the number of $^{13}$C atoms at central positions within hydrocarbon molecules of the hydrocarbon species and the number of $^{13}$C atoms at terminal positions within hydrocarbon molecules of the hydrocarbon species.

7. The method of claim 1, wherein the position specific isotope signature is a position specific isotope signature of propane.

8. The method of claim 1, wherein the clumped isotope signature identifies the ratio of ethane molecules that have two $^{13}$C atoms.

9. The method of claim 1, further comprising running one or more simulations of the model that comprises:
    identifying isotopic sequences of interest;
    identifying a representative group of staring molecules that contain the isotopic sequence of interest;
    identify the proportion or ratio of the starting molecules in the representative group;
    identifying the probability of the cracking reaction occurring to the molecules in the representative group; and
    identifying the molecules to be broken.

10. The method of claim 1, further comprising performing two or more simulations of the model, wherein each simulation uses a different initial molecule population.

11. The method of claim 10, wherein the two or more simulations of the model produce different expected clumped isotope signatures or expected position specific isotope signatures.

12. The method of claim 11, wherein each of the expected clumped isotope signatures or expected position specific isotope signatures is associated with a different hydrocarbon source.

13. The method of claim 12, further comprising comparing the measured clumped isotope signatures or expected position specific isotope signatures with each of the expected clumped isotope signatures or expected position specific isotope signatures, and using the comparison to identify the source from which the hydrocarbon fluid sample was obtained.

14. The method of claim 1, further comprising using the comparison to de-risk a basin model of a hydrocarbon reservoir.

15. A method for determining where to drill a well in a hydrocarbon reservoir, comprising:
    providing a basin model of the hydrocarbon reservoir;
    obtaining a hydrocarbon fluid sample from the hydrocarbon reservoir;
    analyzing the hydrocarbon fluid sample to determine at least one measured clumped isotope signature or measured position specific isotope signature for at least one hydrocarbon species in the hydrocarbon fluid sample;
    determining at least one expected clumped isotope signature or expected position specific isotope signature, where the expected clumped isotope signature or expected position specific isotope signature is determined from a model that reflects different source compositions, isotopic structures, and kinetic processes associated with the hydrocarbon reservoir, and wherein the model is solved using a kinetic Monte Carlo simulation;

comparing the measured clumped isotope signature or measured position specific isotope signature with the expected clumped isotope signature or expected position specific isotope signature;

using the comparison to identify an expected source of the hydrocarbons in the basin model; and causing a well to be drilled to obtain hydrocarbon from the hydrocarbon reservoir.

* * * * *